(12) United States Patent
Van Bibber et al.

(10) Patent No.: US 11,786,357 B2
(45) Date of Patent: *Oct. 17, 2023

(54) DEVICES AND METHODS FOR ANATOMIC MAPPING FOR PROSTHETIC IMPLANTS

(71) Applicant: Bolton Medical, Inc., Sunrise, FL (US)

(72) Inventors: Richard Van Bibber, Redmond, WA (US); Thomas C. Douthitt, Kirkland, WA (US); Arun Palligaranai Tirumalai, Sammamish, WA (US); Prashanth Dumpuri, Kirkland, WA (US)

(73) Assignee: Bolton Medical, Inc., Sunrise, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/486,572

(22) Filed: Sep. 27, 2021

(65) Prior Publication Data
US 2022/0008134 A1 Jan. 13, 2022

Related U.S. Application Data

(63) Continuation of application No. 16/863,316, filed on Apr. 30, 2020, now Pat. No. 11,160,613, which is a
(Continued)

(51) Int. Cl.
*A61F 2/07* (2013.01)
*A61B 34/10* (2016.01)
(Continued)

(52) U.S. Cl.
CPC ............... *A61F 2/07* (2013.01); *A61B 34/10* (2016.02); *G06T 3/0056* (2013.01);
(Continued)

(58) Field of Classification Search
CPC ..... A61B 34/10; A61B 2034/108; A61F 2/07; A61F 2/89; A61F 2002/061;
(Continued)

(56) References Cited

U.S. PATENT DOCUMENTS 5,370,692 A 12/1994 Fink et al.
6,551,341 B2 4/2003 Boylan et al.
(Continued)

FOREIGN PATENT DOCUMENTS

JP 2001/079097 A 3/2001
WO WO-02/29758 A2 4/2002
(Continued)

OTHER PUBLICATIONS

Hazer et al., "A workflow for computational fluid dynamics simulations using patient-specific aortic models," 24th CADFEM Users Meeting 2006, International Congress on FEM Technology with 2006 German ANSYS Conference, Oct. 25, 2006, 9 pages.
(Continued)

*Primary Examiner* — John B Strege
(74) *Attorney, Agent, or Firm* — Stephen J. Kenny; Vincenzo DiMonaco; Foley Hoag LLP

(57) ABSTRACT

A method of generating a patient-specific prosthetic includes receiving anatomic imaging data representative of a portion of a patient's anatomy. A first digital representation of the anatomic imaging data is defined. The first digital representation of the anatomic imaging data is modified. A second digital representation of the portion of the patient's anatomy is defined based on the modifying of the first digital representation of the anatomic imaging data. A patient-specific prosthetic template of the portion of the patient's anatomy is generated based at least in part on the second digital representation of the anatomic imaging data.

10 Claims, 7 Drawing Sheets

Related U.S. Application Data continuation of application No. 15/461,922, filed on Mar. 17, 2017, now Pat. No. 10,653,484, which is a continuation of application No. 15/163,255, filed on May 24, 2016, now Pat. No. 9,629,686, which is a continuation of application No. PCT/US2016/029185, filed on Apr. 25, 2016.

(60) Provisional application No. 62/151,506, filed on Apr. 23, 2015.

(51) Int. Cl.
| | |
|---|---|
| *G06T 3/00* | (2006.01) |
| *G06T 7/00* | (2017.01) |
| *G06T 7/60* | (2017.01) |
| *A61F 2/06* | (2013.01) |
| *A61F 2/89* | (2013.01) |

(52) U.S. Cl.
CPC .............. *G06T 7/0012* (2013.01); *G06T 7/60* (2013.01); *A61B 2034/108* (2016.02); *A61F 2/89* (2013.01); *A61F 2002/061* (2013.01); *A61F 2240/002* (2013.01); *A61F 2240/005* (2013.01); *G06T 2207/30048* (2013.01); *G06T 2219/2004* (2013.01)

(58) Field of Classification Search
CPC ......... A61F 2240/002; A61F 2240/005; G06T 3/0056; G06T 7/0012; G06T 7/60; G06T 2207/30048; G06T 2207/2004; G06V 10/40

See application file for complete search history.

(56) References Cited

U.S. PATENT DOCUMENTS

| | | |
|---|---|---|
| 7,197,170 B2 | 3/2007 | Dwyer et al. |
| 7,937,660 B2 | 5/2011 | Binkert |
| 8,249,815 B2 | 8/2012 | Taylor |
| 8,359,118 B2 | 1/2013 | Ono et al. |
| 8,682,626 B2 | 3/2014 | Ionasec et al. |
| 8,831,302 B2 | 9/2014 | Mahfouz |
| 8,897,513 B2 | 11/2014 | Balasubramanian |
| 8,958,623 B1 | 2/2015 | Grady et al. |
| 8,989,460 B2 | 3/2015 | Mahfouz |
| 9,095,421 B2 | 8/2015 | Peterson |
| 9,305,123 B2 | 4/2016 | Leotta et al. |
| 9,629,686 B2 | 4/2017 | Van Bibber et al. |
| 9,629,705 B2 | 4/2017 | Douthitt et al. |
| 10,653,484 B2 | 5/2020 | Van Bibber et al. |
| 2002/0193872 A1 | 12/2002 | Trout et al. |
| 2003/0195411 A1 | 10/2003 | Sureda et al. |
| 2004/0102866 A1 | 5/2004 | Harris et al. |
| 2005/0131518 A1 | 6/2005 | Hartley et al. |
| 2006/0058638 A1 | 3/2006 | Boese et al. |
| 2007/0293936 A1 | 12/2007 | Dobak |
| 2008/0201007 A1 | 8/2008 | Boyden et al. |
| 2008/0255582 A1 | 10/2008 | Harris |
| 2009/0204228 A1 | 8/2009 | Hiles |
| 2009/0304245 A1 | 12/2009 | Egger et al. |
| 2013/0289690 A1 | 10/2013 | Thapliyal |
| 2013/0296998 A1* | 11/2013 | Leotta .................. G05B 15/02 623/1.11 |
| 2015/0238121 A1 | 8/2015 | Tu et al. |
| 2015/0332455 A1 | 11/2015 | Kobayashi et al. |
| 2016/0247279 A1 | 8/2016 | Lavi et al. |
| 2020/0390499 A1 | 12/2020 | Van Bibber et al. |

FOREIGN PATENT DOCUMENTS

| | | |
|---|---|---|
| WO | WO-2007045000 A2 | 4/2007 |
| WO | WO-2008/124222 A1 | 10/2008 |
| WO | WO-2014/53616 A1 | 4/2014 |

OTHER PUBLICATIONS

Higashiura et al., "Initial experience of branched endovascular graft for abdominal aortic aneurysm with complex anatomy of proximal neck: planning and technical considerations," Jpn J Radiol, 28:66-74 (2010).

Legget et al., "System for quantitative three-dimensional echocardiography of the left ventricle based on a magnetic-field position and orientation system," IEEE Transactions on Biomedical Engineering, 45(4):494-504 (1998).

Leotta et al., "Measurement of abdominal aortic aneurysms with three-dimensional ultrasound imaging: preliminary report," Journal of Vascular Surgery, 33(4):700-707 (2001).

Malina et al., "EVAR and complex anatomy: an update on fenestrated and branched stent grafts," Scandinavian Journal of Surgery, 97:195-204 (2008).

Nordon et al., "Toward an 'off-the-shelf' fenestrated endograft for management of short-necked abdominal aortic aneurysms: an analysis of current graft morphological diversity," J Endovasc Ther., 17:78-85 (2010).

Notice of Allowance for U.S. Appl. No. 15/163,255 dated Mar. 1, 2017.

Notice of Allowance for U.S. Appl. No. 15/461,922 dated Jan. 22, 2020.

Oderich et al., "Modified fenestrated stent grafts: device design, modifications, implantation, and current applications," Perspectives in Vascular Surgery and Endovascular Therapy, 21(3):157-167 (2009).

Office Action dated Feb. 12, 2019 from U.S. Appl. No. 15/461,922, 8 pages.

Office Action dated Sep. 20, 2016 from U.S. Appl. No. 15/163,255, 10 pages.

Resch et al., "Incidence and management of complications after branched and fenestrated endographing," Journal of Cardiovascular Surgery, 51(1):105-113 (2010).

Ricotta et al., "Fenestrated and branched stent grafts," Perspective Vascular Surgery and Endovascular Therapy, 20(2):174-187 (2008).

Stratasys, Dimension 1200es 3D modeling printer, Durability Meets Affordability, www.stratasys.com/3d-printers/design-series/performance/dimension-1200es, 2014, 4 pages.

UK Evar Trial Investigators, "Endovascular versus open repair of abdominal aortic aneurysm," New England Journal of Medicine, May 20, 2010, vol. 362, No. 20, pp. 1863-1871.

* cited by examiner

DEVICES AND METHODS FOR ANATOMIC MAPPING FOR PROSTHETIC IMPLANTS

CROSS-REFERENCE TO RELATED APPLICATIONS

This application is a continuation of U.S. patent application Ser. No. 16/863,316, filed Apr. 30, 2020, which is a continuation of U.S. patent application Ser. No. 15/461,922, filed Mar. 17, 2017, now U.S. Pat. No. 10,653,484, which is a continuation of U.S. patent application Ser. No. 15/163,255, filed May 24, 2016, now U.S. Pat. No. 9,629,686, which is a continuation of International Patent Application No. PCT/US2016/029185, Apr. 25, 2016, which claims priority to and the benefit of U.S. Provisional Patent Application No. 62/151,506, filed Apr. 23, 2015, the disclosures of which are hereby incorporated by reference in their entireties.

BACKGROUND

The embodiments described herein relate generally to prosthetic implants and more particularly, to devices and methods for mapping projected changes in anatomic features resulting from the placement of a prosthetic implant.

Prosthetic devices are often implanted into, for example, diseased portions of a patient to repair, support, stent, and/or otherwise facilitate the proper function of those diseased portions. In some instances, prosthetic devices such as stent grafts can be used to repair diseased portions of a patient's vascular system. For example, aneurysms within a patient's vascular system generally involve the abnormal swelling or dilation of a blood vessel such as an artery, which typically weakens the wall of the blood vessel making it susceptible to rupture. An abdominal aortic aneurysm (AAA) is a common type of aneurysm that poses a serious health threat. A common way to treat AAA and other types of aneurysms is to place an endovascular stent graft in the affected blood vessel such that the stent graft spans across (e.g., traverses) and extends beyond the proximal and distal ends of the diseased portion of the vasculature. The stent graft can thus, reline the diseased vasculature, providing an alternate blood conduit that isolates the aneurysm from the high-pressure flow of blood, thereby reducing or eliminating the risk of rupture. In other instances, a prosthetic device can be an implant and/or mechanism, which can provide structural or functional support to a diseased and/or defective portion of the body. In some instances, however, the arrangement of the anatomy can present challenges when attempting to place and/or secure a prosthetic device (including stent grafts or the like). Such challenges can result in misalignment and/or suboptimal configuration of the prosthetic device within the anatomy.

Therefore, a need exists for improved devices and methods for mapping projected changes in anatomic features resulting from the placement of a prosthetic implant.

SUMMARY

Devices and methods for improving the fenestration process of stent grafts are described herein. In some embodiments, a method of generating a patient-specific prosthetic includes receiving anatomic imaging data representative of a portion of a patient's anatomy. A first digital representation of the anatomic imaging data is defined. The first digital representation of the anatomic imaging data is modified. A second digital representation of the portion of the patient's anatomy is defined based on the modifying of the first digital representation of the anatomic imaging data. A patient-specific prosthetic template of the portion of the patient's anatomy is generated based at least in part on the second digital representation of the anatomic imaging data.

DETAILED DESCRIPTION

Figure 1:
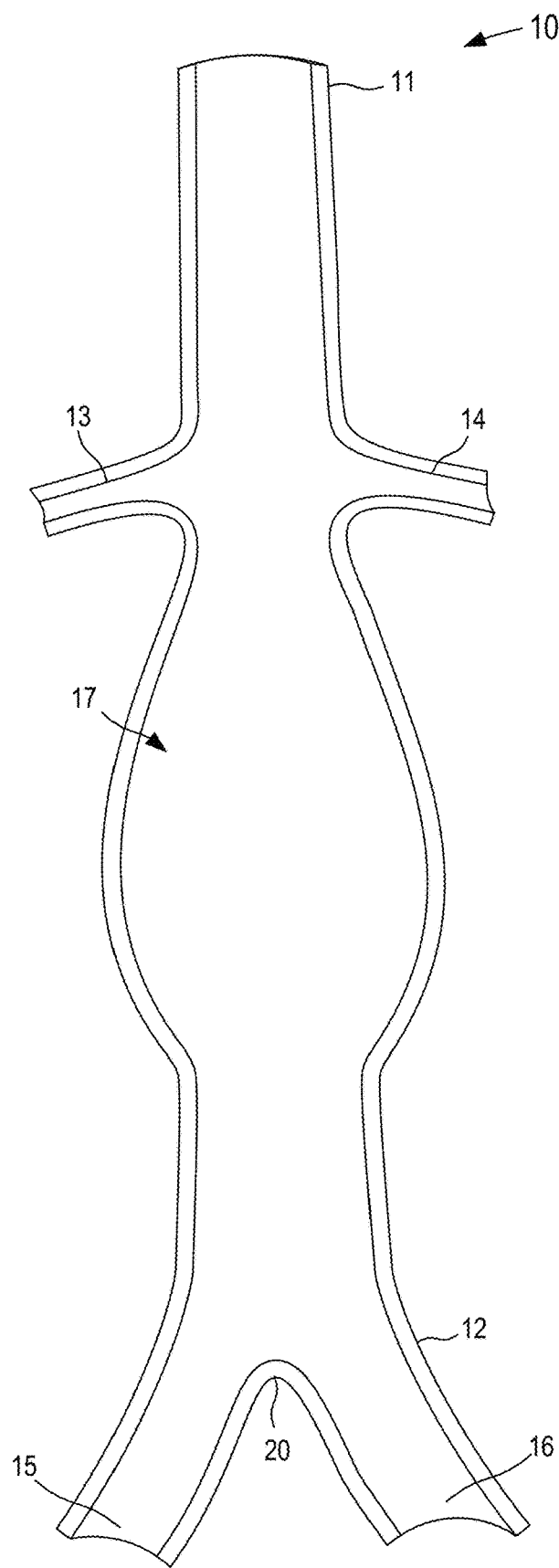
FIG. 1 is an illustration of a diseased abdominal aorta according to an embodiment.

Devices and methods for improving the fenestration process of stent grafts are described herein. In some embodiments, a method of forming a patient-specific prosthetic includes receiving anatomic imaging data representative of a portion of a patient's anatomy. A first digital representation of the anatomic imaging data is defined. The first digital representation of the anatomic imaging data is modified. A second digital representation of the portion of the patient's anatomy is defined based on the modifying of the first digital representation of the anatomic imaging data. A patient-specific prosthetic template of the portion of the patient's anatomy is formed based at least in part on the second digital representation of the anatomic imaging data.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the words "proximal" and "distal" refer to a direction closer to and away from, respectively, an operator of, for example, a medical device. Thus, for example, the end of the medical device contacting the patient's body would be the distal end of the medical device, while the end opposite the distal end would be the proximal end of the medical device. Similarly, when a device such as an endovascular stent graft is disposed within a portion of the patient, the end of the device closer to the patient's heart would be the proximal end, while the end opposite the proximal end would be the distal end. In other words, the proximal end of such a device can be upstream of the distal end of the device.

The embodiments described herein can be formed or constructed of one or more biocompatible materials.

Examples of suitable biocompatible materials include metals, ceramics, or polymers. Examples of suitable metals include pharmaceutical grade stainless steel, gold, titanium, nickel, iron, platinum, tin, chromium, copper, and/or alloys thereof. Examples of polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, polyethylene terephthalate (PET), polytetrafluoroethylene (PTFE), and/or blends and copolymers thereof.

The embodiments described herein can be used to facilitate the function and/or the integration of a prosthetic device within a portion of a patient. For example, in some embodiments, the devices and/or methods described herein can be used in conjunction with and/or can otherwise be included endovascular repair using stent grafts. Although the embodiments are shown and described herein as being used, for example, to facilitate endovascular repair, in other embodiments, any of the devices and/or methods described herein can be used to facilitate treatment of any portion of a patient. For example, the devices and methods described herein can facilitate the integration of any suitable implant, prosthetic, device, mechanism, machine, and/or the like within a portion of the body of a patient such as the patient's vascular system, nervous system, muscular-skeletal system, etc. Therefore, while the embodiments are shown and described herein as being used in the endovascular repair of an abdominal aortic aneurysm, they are presented by way of example and are not limited thereto.

Some of the devices and/or methods described herein can be used in minimally invasive treatment techniques such as endovascular repair using stent grafts. Such repair techniques are generally preferred over traditional open surgical repair and often result in reduced morbidity or mortality rates. In some instances, however, the arrangement of the diseased vasculature can result in a need to alter a portion of the stent graft prior to insertion into the body. For example, in an endovascular repair of an abdominal aortic aneurysm, the aneurysm can be situated adjacent to and/or directly distal to normally functioning vessels branching from a portion of the aorta. In order to reline the aneurysm with the stent graft, surgeons often cut openings in the stent graft fabric to accommodate specific branch vessel origins, a process known as "fenestration". Specifically, in treating juxtarenal aneurysms, for instance, the fenestrations or openings of the stent grafts can correspond to a size, shape, and/or relative position of, inter alia, the renal arteries.

Traditionally, the fenestration process involves measurements based on medical images (such as CT scans) of the vessel origins. For example, in some instances, longitudinal distances of branch vessels can be measured and relative angular locations of the branch vessels can be estimated and/or calculated from a reference point. Based on these measurements and/or calculations, a surgeon can mark and cut the stent fabric of a stent graft to define one or more fenestrations. The fenestrated stent graft can then be positioned within the diseased vasculature (e.g., via an endovascular procedure) and oriented to substantially align the fenestrations with openings of the corresponding branch vessels.

In some instances, the devices and/or methods described herein can be used to generate a template and/or model based on medical imaging data of a diseased portion of a patient's vascular system (e.g., an abdominal aortic aneurysm). In some embodiments, the template can be substantially similar to those described in U.S. Patent Publication No. 2013/0296998 entitled, "Fenestration Template for Endovascular Repair of Aortic Aneurysms," filed May 1, 2013 ("the '998 publication"), the disclosure of which is incorporated herein by reference in its entirety. For example, an electronic device such as a personal computer, workstation, laptop, etc. can receive the imaging data and can calculate and/or otherwise define a digital representation of the imaging data. Based on the digital representation, the electronic device can define the template and can send a signal to an output device such as a 3-D printer or rapid prototyping device, which can then output, form, and/or 2-D or 3-D print the template. The template, in turn, can be used to facilitate the fenestration process of a prosthetic (e.g., a stent graft). Moreover, the devices and/or methods described herein can be used to determine and/or calculate a change in the arrangement of a portion of the anatomy resulting from the insertion and/or indwelling of the prosthetic, and can form a template representing the portion of the anatomy thereafter, as described in further detail herein.

Figure 2A:
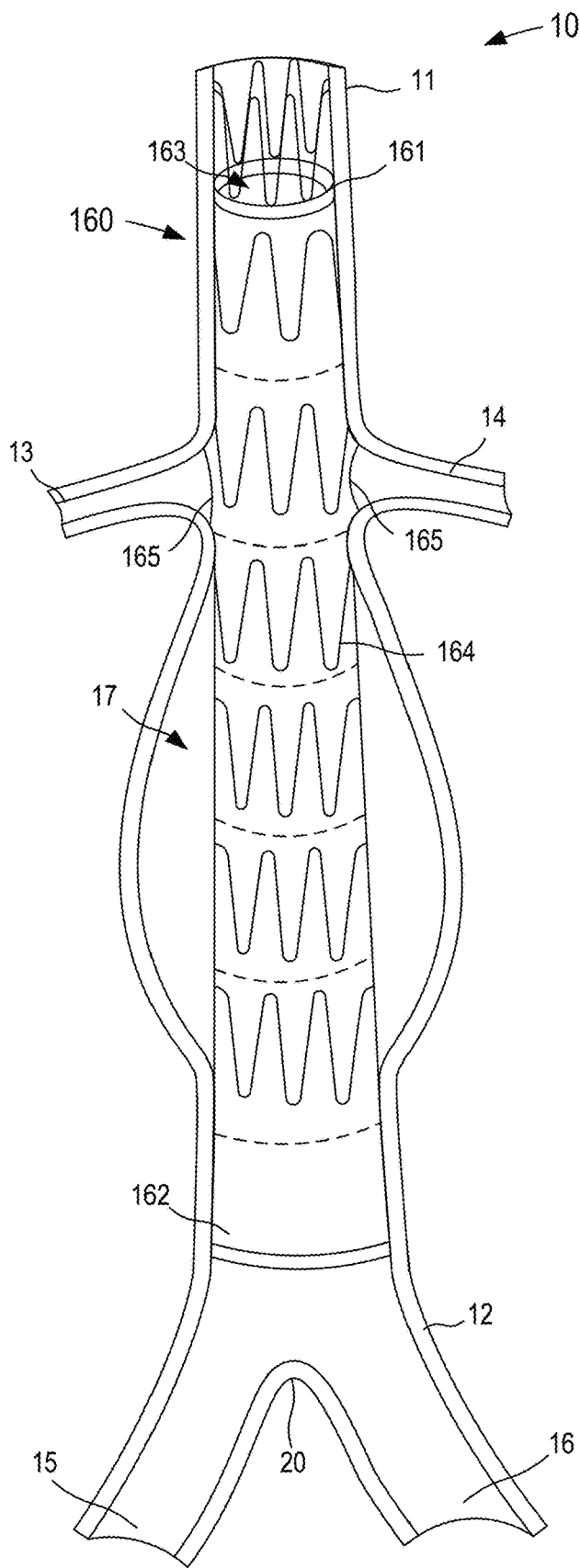
FIG. 2A is a portion of a stent graft according to an embodiment and directly after placement within the diseased abdominal aorta of FIG. 1.
Figure 2B:
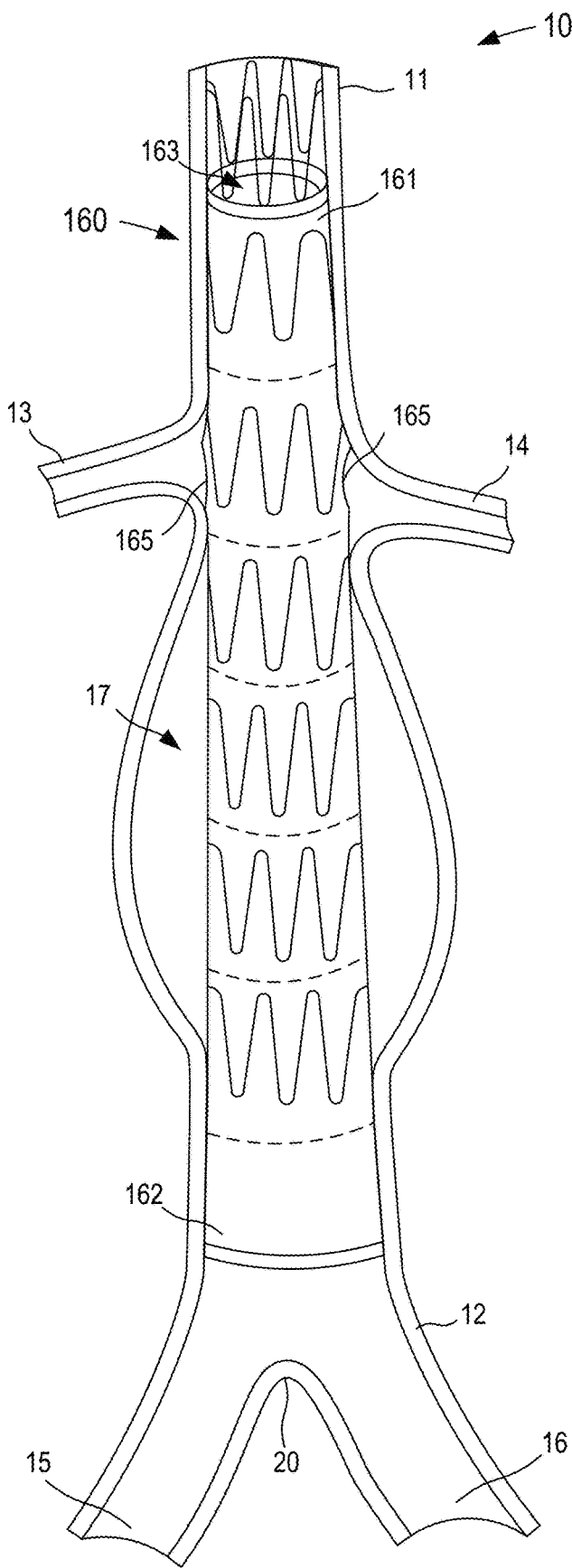
FIG. 2B is a portion of the stent graft of FIG. 2A and placed within the diseased abdominal aorta of FIG. 1 and after a time of indwelling.

FIGS. 1-2B illustrate a diseased portion of a patient's abdominal aorta 10. While portions of the abdominal aorta 10 are described below, the discussion of the abdominal aorta 10 is not exhaustive; rather, the discussion below provides a reference to the relevant anatomic structures. The abdominal aorta 10 (also referred to herein as "aorta") has a proximal end portion 11, receiving a flow of blood from the descending aorta (not shown), and a distal end portion 12, supplying a flow of blood to the lower limbs. As shown in FIG. 1, the aorta 10 at or near the proximal end portion 11 supplies a flow of blood to the left renal artery 14 and the right renal artery 13, which in turn, supply blood to the left and right kidney, respectively. Although not shown in FIG. 1, the proximal end portion 11 of the aorta 10 also supplies a flow of blood to the superior mesenteric artery (SMA) and the celiac artery. The distal end portion 12 of the aorta 10 forms the iliac bifurcation 20, through which the aorta 10 supplies a flow of blood to the left common iliac artery 16 and the right common iliac artery 15, which in turn, supply blood to the left and right lower limbs, respectively. As shown in FIG. 1, this patient has an abdominal aortic aneurysm (AAA) 17 positioned distal to the renal arties 13 and 14 and proximal to the iliac bifurcation 20. More specifically, the AAA 17 is disposed in a position that precludes the attachment of a proximal end portion of a stent graft between the renal arteries 13 and 14 and the AAA 17, and thus, a fenestrated stent graft 160 (see e.g., FIGS. 2A and 2B) is used for endovascular repair of the AAA 17.

In some instances, endovascular repair of the AAA 17 includes scanning and/or otherwise capturing anatomic imaging data associated with the patient's aorta 10. For example, an imaging device can be a X-ray device, a computed tomography (CT) device, a computed axial tomography (CAT) device, a magnetic resonance imaging device (MRI), a magnetic resonance angiograph (MRA) device, a positron emission tomography (PET) device, a single photon emission computed tomography (SPECT) device, an ultrasound device, and/or any other suitable device for imaging a portion of the patient and/or a combination thereof (e.g., a CT/MRA device, a PET/CT device, a SPECT/CT device, etc.). The imaging data captured by the imaging device can thus, be used to determine salient features of the patient's aorta 10 such as, for example, the branch vessels in fluid communication with the aorta 10. For example, a doctor, surgeon, technician, etc. can use the imaging data to determine and/or calculate a size, shape, position, and/or orientation of at least the renal arteries 13 and 14. In some instances, the doctor, surgeon, technician, etc. can form and/or define one or more fenestrations 165 in the stent graft 160 associated with the determined and/or calculated characteristics of at least the renal arteries 13 and 14. In other instances, the imaging data can be used to form and/or define a template or the like that can define a set of openings and/or otherwise include a set of indicators associated with at least the renal arteries 13 and 14. The template can then be used to define the fenestrations 165 in the stent graft 160.

As shown in FIG. 2A, the stent graft 160 can be positioned within a portion of the patient's abdominal aorta 10 via an endovascular procedure. For example, the stent graft 160 can be disposed within a delivery catheter (e.g., in a collapsed, compressed, restrained, and/or otherwise un-deployed configuration), which is inserted into, for example, the femoral artery (not shown). The delivery catheter can be advanced through the artery and into the abdominal aorta 10. Once advanced to a desired position within the abdominal aorta 10, the delivery catheter can be withdrawn relative to the stent graft 160. As the delivery catheter is retracted and/or withdrawn, the stent graft 160 transitions from the collapsed configuration to an expanded or deployed configuration, thereby stenting a portion of the abdominal aorta 10.

The stent graft 160 includes a proximal end portion 161 and a distal end portion 162 and defines a lumen therethrough 163. The stent graft 160 can be any suitable stent graft. For example, the stent graft 160 can be formed from a resilient, biocompatible material such as those described above. In some embodiments, the stent graft 160 can be formed from a polytetrafluoroethylene (PTFE) or polyethylene terephthalate (PET or Dacron®). The stent graft 160 also includes a set of stiffening members 164 disposed circumferentially about the stent graft 160. The stiffening members 164 can be any suitable structure that can, for example, bias the stent graft 160 in an open configuration, thereby structurally supporting the stent material (also known as "stent fabric"). In some embodiments, the stiffening members 164 can be formed from a metal or a metal alloy such as, for example, those described above. In some embodiments, such a metal or metal alloy, for example, is radio-opaque and/or otherwise coated with a radio-opaque material configured to be visible using, for example, fluoroscopy. The stiffening members 164 can transition from a restrained or deformed delivery configuration (e.g., when disposed in a delivery catheter to an expanded and/or biased indwelling configuration, as shown in FIG. 2A.

In this embodiment, the stent graft 160 defines the set of fenestrations 165, as described above. The fenestrations 165 are each aligned with its corresponding renal artery 13 or 14 and can each have a size, shape, and/or configuration that is associated with its corresponding renal artery 13 or 14. In this manner, the fenestrations 165 can allow blood to flow from the aorta 10 and into the left renal artery 14 and the right renal artery 13 via the fenestrations 165. Although not shown in FIG. 2A, the stent graft 160 can define one or more fenestrations associated with other branch vessels stemming from the aorta 10 such as, for example, the superior mesenteric artery (SMA), the celiac artery, and/or the like.

As shown in FIG. 2B, the placement and/or indwelling of the stent graft 160 within the aorta 10 can, for example, alter, shift, rotate, translate, morph, and/or otherwise reconfigured the arrangement of the patient's aorta 10. As a result, the openings of the renal arteries 13 and 14 are shifted relative to the fenestrations 165 defined by the stent graft 160. In some instances, the shifting of the aorta 10 relative to the stent graft 160 results in at least a partial blockage of the renal arteries 13 and 14, as shown in FIG. 2B. For example, in some instances, the openings of the renal arteries 13 and 14 can be about 4 millimeters (mm) to about 7 mm, and the shifting and/or rearrangement of the aorta 10 can result in a shifting of the openings of the renal arteries 13 and 14 relative to the fenestrations 165 by about 1 mm, about 2 mm, about 3 mm, about 4 mm, about 5 mm, about 6 mm, about 7 mm, or more. Thus, despite defining the fenestrations 165 in a position along the stent graft 160 based on the imaging data, the shifting of the aorta 10 resulting from the placement and/or indwelling of the stent graft 160 can result in a blockage of the renal arteries 13 and 14. In some instances, the shifting of the aorta 10 can result in more than about a 1%, 5%, 10%, 20%, 30%, 40%, 50%, 60%, 70%, 80%, 90%, or 100% blockage of the renal arteries 13 and 14. Although not shown in FIGS. 2A and 2B, the shifting of the aorta 10 can result in a similar misalignment of any branch vessel relative to its corresponding fenestration in the stent graft 160.

In some embodiments, an electronic device can be configured to determine and/or calculate the shift in the anatomy that would result from the insertion and/or indwelling of prosthetic (e.g., a stent graft) and can define one or more digital representations of the anatomy. For example, the electronic device can be a personal computer (PC), a laptop, a workstation, and/or the like disposed in a central location or distributed in multiple locations. The electronic device can include at least a processor and a memory. In some embodiments, the electronic device can also include a display and/or the like. The memory can be, for example, a random access memory (RAM), a memory buffer, a hard drive, a database, an erasable programmable read-only memory (EPROM), an electrically erasable read-only memory (EEPROM), a read-only memory (ROM), a solid-state drive (SSD), and/or the like. The processor can be any suitable processor configured to run and/or execute a set of instructions, for example, stored in the memory. For example, the processor can be a general-purpose processor, a Field Programmable Gate Array (FPGA), an Application Specific Integrated Circuit (ASIC), a Digital Signal Processor (DSP), a central processing unit (CPU), an accelerated processing unit (APU), a front-end processor, a graphics-processing unit (GPU), and/or the like. In some embodiments, the memory can store instructions and/or code to cause the processor to execute modules, processes and/or functions associated with determining the shift in the anatomy, defining a digital representation of the shifted anatomy, and/or forming a fenestration template, as described in further detail herein. In addition, the memory can be configured to store data (e.g., in a database) such as imaging data, patient data, data associated with the digital representation of the anatomy, data associated with the fenestration template, etc.

As described above, the electronic device can be used to receive imaging data of a portion of a patient's anatomy and can determine and/or calculate a change in the portion of the patient's anatomy that can result from the implantation of a prosthetic. In addition, the electronic device can be configured to define a digital representation of the portion of the patient's anatomy before and/or after the change in the portion of the anatomy. Based on the digital representation of the portion of the patient's anatomy, the electronic device can define a fenestration template, which in turn, can be used to form and/or define fenestrations in the stent fabric of a stent graft. For example, an imaging device can be configured to capture and/or scan imaging data associated with a patient's anatomy, as described above. The electronic device is configured to receive the imaging data and can store it, for example, in the memory. For example, the electronic device can be in communication with the imaging device via a network, or the like. In other embodiments, a user can cause the imaging data to be saved to the memory and/or the like.

Once the electronic device receives the imaging data, the electronic device can perform any number of processes and/or functions associated with analyzing the imaging data to define the digital representation (also referred to herein as "model") of the imaging data. In some embodiments, the electronic device can be configured to present the model of the imaging data on a display and/or the like. In this manner, the electronic device can, for example, graphically represent an accurate anatomic model of the portion of the patient (e.g., the abdominal aorta). In some instances, the electronic device can, for example, determine salient anatomic features and can identify them in the model. The electronic device can then define a digital representation that includes only those salient anatomic features, thereby reduces processing load and/or file size. The electronic device can also store any suitable digital representation in the memory and can, for example, associate the digital representations with the patient (e.g., in a database).

In some instances, based on the model of the imaging data, a portion of the model of the imaging data, the model of the salient anatomic features, and/or a combination thereof, the electronic device can define, for example, a prosthesis template. Specifically, as described herein, the electronic device can define a fenestration template configured to facilitate the fenestration process of a stent graft according to the patient's anatomy. Such a fenestration template can include openings (fenestrations), protrusions, markers, indicators, frangible portions, and/or any other suitable feature corresponding to, for example, the openings of the aorta leading to the branch vasculature, as described in further detail herein. In some embodiments, the template can be substantially similar to any of those described in the '998 publication, incorporated by reference above.

In some instances, the electronic device can also perform one or more processes to adjust, modify, change, update, augment, morph, and/or otherwise alter the data associated with the model to define an updated model based on a set of characteristics associated with at least one of the patient, the prosthesis (e.g., the stent graft), and/or a manner in which the prosthesis will be delivered. For example, as described above, the electronic device can be configured to define an updated model based on the effects of the placement of the prosthesis and its indwelling within, for example, the aorta. Said another way, because the anatomy of at least the abdominal aorta changes when a stent graft is disposed therein and/or while it is being positioned therein, the electronic device is configured to adjust the data associated with the model to account for such changes based on characteristics associated with the patient, the stent graft, and/or the delivery method.

For example, in addition to a mapping (e.g., location information or topography) of the patient's anatomy, the imaging data can also include information related to any other discernable characteristic identified by the imaging technique. Specifically, the imaging data can include, inter alia, a degree of aortic angulation at the juxtarenal neck or other segment of the aorta; a degree, pattern, and location of atherosclerotic disease including plaque, calcification, and/or thrombus; morphometric characteristics of the vascular structure that influence size, position, angulation, or tortuosity such as vessel diameter (i.e., vascular lumen diameter); and/or vessel wall thickness, vessel length, location and number of branch arteries, and/or the like. In some embodiments, the electronic device can extract data associated with these characteristics and can store the extracted data in the memory. Moreover, the extracted data can be stored with and/or otherwise associated with other stored patient data and/or stored prosthetic data. For example, the electronic device can store anthropomorphic data of the patient such as body composition, body temperature, height, weight, body-mass index (BMI), abdominal circumference (absolute or normalized), age, and/or the like; pre-existing vascular or extravascular prostheses or foreign bodies; impact of specific delivery methods such as use of guide wires, catheters, and/or the like; degree of oversizing of the prostheses required to achieve stability; mechanical properties of the prosthesis such as, for example, body material or fabric type, stent or support strut geometry and/or thickness, type of metals or other support materials, stiffness and diameter of the prosthesis and/or devices used to deliver the prosthesis; and/or the like.

In some instances, the electronic device can determine, evaluate, and/or otherwise calculate a weight, value, score, percentage, scale value, influence measure, impact measure, importance measure, and/or any other suitable quantifiable evaluation of the data associated with the aforementioned characteristics. Specifically, the electronic device can perform one or more processes, calculations, evaluations, etc. to determine a quality or measure of impact of the identified characteristics. For example, in some instances, a first amount of angulation of a juxtarenal neck can be greater than a second amount of angulation of a juxtarenal neck. Thus, when a greater angulation of the juxtarenal neck is indicative of and/or otherwise corresponds to a shifting and/or changing of the aortic arrangement resulting from the placement of a stent graft, the first amount of angulation can be associated with a greater value, score, weight, measure, etc., than the second amount of angulation.

Expanding further, in at least one embodiment, the electronic device can perform such an analysis based on, for example, a weighted analysis in which characteristics and/or factors resulting in a greater amount of shifting of the aortic anatomy are associated with a greater weighting than those that affect a lesser amount of shifting. For example, the weighting of the characteristics can be associated with a value (e.g., a multiplier or the like) such as, for example, a percentage represented in decimal format between zero and one (e.g., 10% represented as 0.1, 25% represented as 0.25, 50% represented as 0.5, etc.). In other instances, the percentages used in a weighted analysis can be 100% or greater represented in decimal format (e.g., 125% represented as 1.25, 175% represented as 1.75, 200% represented as 2.0, etc.). In still other instances, the weighted analysis can be based on any suitable scoring system or scale such as, for example, 1-10, 1-100, 1-1000, etc. including whole numbers or fractions thereof.

In some instances, a first set of characteristics can have a greater weight than a second set of characteristics. For example, in some embodiments, the characteristics extracted from the imaging data can, as a group, have a higher weight than the set of characteristics associated with, for example, method of placing the stent graft, as a group. In this manner, the electronic device can perform any suitable evaluation, calculation, determination, etc. of the set of characteristics associated with the prosthesis (e.g., the stent graft), the patient, and/or the delivery method of the prosthesis. Moreover, while specific examples of a weighting system are described, in other embodiments, the electronic device can perform any suitable weighting and/or evaluating technique. In some embodiments, the characteristics are generally associated with a numerical measure (e.g., a stiffness of the prosthesis is a calculable value based on the properties of the material); thus, the electronic device can be configured to use the "intrinsic" or predetermined values in a predefined equation or the like. Thus, by quantifying such characteristics, the electronic device can adjust and/or update the data associated with the model to define an updated model based on an anticipated, predicted, predetermined, calculated, and/or otherwise probable shift in the arrangement resulting from the insertion and indwelling of the endovascular stent graft. Said another way, the model can be based on a predetermined data set, and the predetermined data set can be updated based on data associated with an anticipated, predicted, predetermined, calculated, and/or otherwise probable shift in the arrangement resulting from the insertion and indwelling of the endovascular stent graft. In some instances, the electronic device can present the updated model on a display or the like.

In some instances, based on the updated model of the imaging data, a portion of the updated model of the imaging data, the model of the salient anatomic features and/or a an updated model of the salient anatomic features, and/or combination thereof, the electronic device can define, for example, a prosthesis template. Specifically, as described herein, the electronic device can define a fenestration template configured to facilitate the fenestration process of a stent graft according to the patient's anatomy. Such a fenestration template can include openings (fenestrations), protrusions, markers, indicators, frangible portions, and/or any other suitable feature corresponding to, for example, the projected, anticipated, adjusted, and/or otherwise calculated location of the openings of the aorta leading to the branch vasculature, as described in further detail herein.

In some instances, the electronic device can include and/or can be in communication with an output device configured to form the template. For example, the output device can be a printer, a rapid prototype machine, a computer numerical controlled (CNC) machine, and/or the like. For example, in some embodiments, the output device is a three-dimensional (3-D) printer configured as and/or otherwise implementing stereolithography (SLA), ink jet systems (e.g., PolyJet, MultiJet, and/or the like), fused deposition modeling (FDM), selective laser sintering (SLS), and/or the like. In such embodiments, the output device can receive a signal from the electronic device indicative of an instruction to produce a 3-D printed output. Specifically, the electronic device can send instructions to cause the output device to 3-D print a fenestrated template used when forming the fenestrated stent graft.

Figure 3:
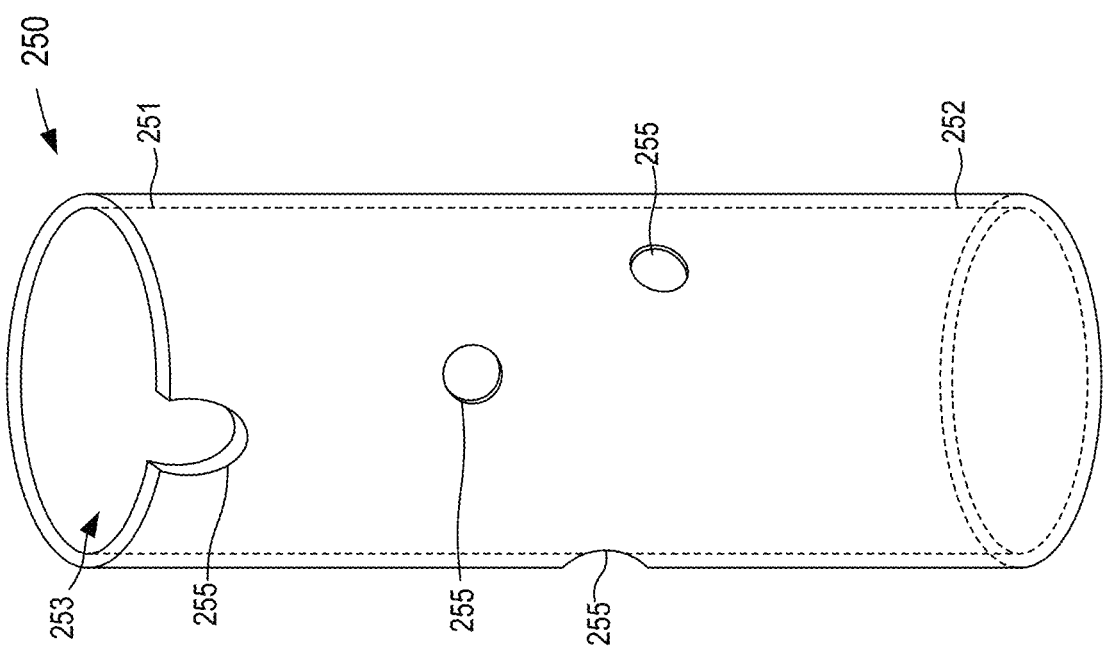
FIG. 3 is an illustration of at least a portion of a fenestration template according to an embodiment.

FIG. 3 illustrates an example of a fenestration template 250 according to an embodiment. In some instances, the fenestration template 250 can be formed, for example, via the process described above and used to generate and/or locate fenestrations on a stent graft. More specifically, in some embodiments, the output device can be a 3-D printer and/or other suitable rapid prototype machine configured to print the fenestration template 250. The fenestration template 250 can be formed from any suitable biocompatible material such as those described herein. The fenestration template 250 includes a proximal end portion 251 and a distal end portion 252, and defines a lumen 253 and a set of fenestrations 255. Generally, the shape, diameter, length, etc. of the fenestration template 250 corresponds to the calculated arrangement of the lumen of the aorta segment represented by the updated model. In other words, the fenestration template 250 corresponds to the updated model defined by the electronic device, which in turn, corresponds to a calculated, projected, and/or modified arrangement of the aorta in response to the insertion and indwelling of, for example, the endovascular stent graft. Hence, a fenestration template 250 generally has a tubular or cylindrical shape. In some embodiments, such as illustrated in FIG. 3, the fenestration template 250 can define the lumen 253 that substantially corresponds to a calculated arrangement of the lumen of the aorta. In some instances, the diameter of the lumen 253 is at least partially based on a diameter of the stent graft to be positioned within the patient. Although the fenestration template 250 is shown and described above as defining the lumen 253 (e.g., is hollow and/or substantially annular), in other embodiments, the fenestration template 250 can be substantially solid and the fenestrations 255 can be, for example, semi-blind, as shown and described in detail in the '998 publication.

The fenestrations 255 are defined along the fenestration template 250 such that each fenestration 255 corresponds to a calculated position of the corresponding branch vasculature such as, for example, the renal arteries. In addition, the fenestration template 250 defines and/or can optionally define one or more fenestrations 255 corresponding to one of the SMA, the celiac artery, and/or any other branch vasculature. In addition, the diameters of the fenestrations 255 defined by the fenestration template can substantially correspond to the actual or calculated diameters of the openings of the branch vessels in fluid communication with a patient's aorta (see e.g., FIGS. 1-2B). In other embodiments, the fenestrations 255 can have a predefined diameter, for example, between about 2 mm and about 10 mm. While the fenestration template 250 is shown as having four fenestrations 255, the position and/or number of the fenestrations 255 can be arranged in any suitable manner corresponding to the calculated position and/or number, respectively, of the branch openings defined by the patient's aorta. Thus, the fenestration template 250 can provide a model and/or template used to locate a corresponding set of fenestrations in a stent graft or the like, as described in further detail herein.

While the fenestration template 250 is shown and described as defining the set of fenestrations 255, in other embodiments, a fenestration template can include a set of markers, indicators, protrusions, spikes, recesses, bumps, and/or any other suitable discontinuity configured to indicate a desired location (e.g., a calculated location) of a fenestration along a stent graft. In some embodiments, the fenestration template 250 can be formed from multiple materials. For example, one or more portions of the fenestration template 250 that correspond with the fenestrations 255 can be formed from a material substantially different from the remaining portions of the fenestration template 250. Such a material can have substantially different mechanical properties than the mechanical properties of a material forming the other portions of the fenestration template 250. For example, such materials can form a frangible portion or an otherwise deformable portion corresponding to the fenestrations 255.

Figure 4:
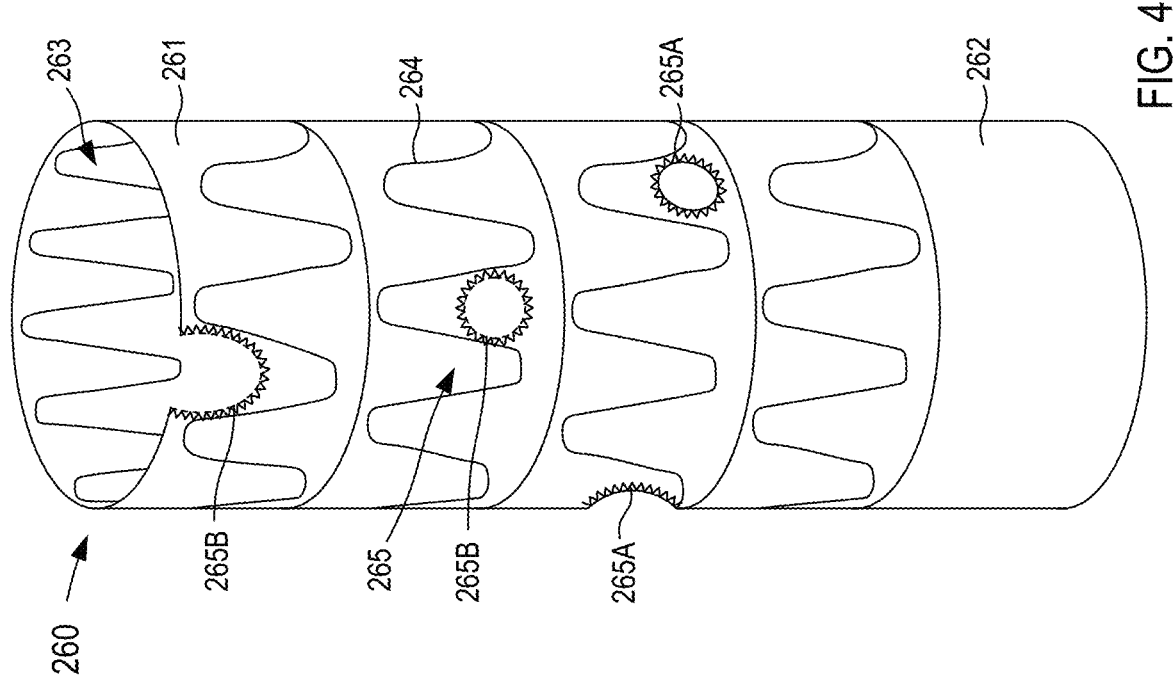
FIG. 4 is an illustration of at least a portion of a fenestrated stent graft according to an embodiment and formed via the fenestration template of FIG. 3.

As described above, the fenestration template 250 can be used, for example, as a guide to form a set of fenestrations in a stent graft used for endovascular repair of an abdominal aortic aneurysm (see e.g., FIGS. 1-2B). By way of example, FIG. 4 illustrates at least a portion of a fenestrated stent graft 260 according to an embodiment. As described above, a stent graft can define one or more fenestrations configured to accommodate one or more branch vessels when the stent graft is deployed in an aorta. Specifically, in this embodiment, the fenestrated stent graft 260 includes a proximal end portion 261 and a distal end portion 262, and defines a lumen 263. The fenestrated stent graft 260 can be any suitable stent graft and/or prosthetic. For example, in some embodiments, the fenestrated stent graft 260 can be an off-the-shelf stent graft. In other embodiments, the fenestrated stent graft 260 can be a patient-specific stent graft with a size, shape, and/or configuration corresponding to the patient's anatomy.

The fenestrated stent graft 260 can have any suitable shape, size, and/or configuration. For example, in some embodiments, the stent graft 260 can have a size that is associated with a size of the lumen defined by the aorta. In other embodiments, the fenestrated stent graft 260 can have a size that is associated with an adjusted or calculated size of the lumen defined by the aorta resulting from the endovascular placement of the fenestrated stent graft 260. Moreover, the fenestrated stent graft 260 can have any suitable mechanical properties such as, for example, strength, stiffness, etc. As shown in FIG. 4, in some embodiments, the fenestrated stent graft 260 can include a set of stiffening members 264 disposed about the fenestrated stent graft 260, which can, for example, increase a stiffness fenestrated stent graft 260.

As described above, the fenestrated stent graft 260 can be positioned relative to the fenestration template 250 such that the fenestration template 250 can mark, guide, indicate, and/or otherwise provide a template for making a set of fenestrations 265 in the fenestrated stent graft 260. For example, in some embodiments, the fenestrated stent graft 260 can be inserted into the lumen 253 defined by the fenestration template 250 and positioned in a desired position relative thereto. In some embodiments, adjustment may be made to the relative positions of the fenestrated stent graft 260 and/or the fenestration template 250 to optimize the fenestration process. For example, the fenestrated stent graft 260 and/or fenestration template 250 may be moved along a longitudinal axis and/or rotated relative to each other about the longitudinal axis to avoid placement of fenestrations 255 defined by the fenestration template 250 over the stiffening members 264. In some embodiments, the fenestrations 265 can be made with the fenestration template 250 still engaged with and/or coupled to the fenestrated stent graft 260. For example, the fenestrations 255 defined by the fenestration template 250 can provide a guide or outline along the fenestrated stent graft 260, which in turn, can be cut (e.g., with a blade, a laser, a water jet, etc.), punched, drilled, and/or the like. In other embodiments, the locations of the fenestrations 265 can be marked, for example, with a sterile pen or other marking devices on the fenestrated stent graft 260 (e.g., through the fenestrations 255 defined by the fenestration template 250) and the actual fenestrations 265 can be defined at the marked locations after the fenestration template 250 is decoupled and/or removed from the fenestrated stent graft 260.

While the fenestrated stent graft 260 is described above as being inserted into the lumen 253 of the fenestration template 250, in other embodiments, the fenestrated stent graft 260 can be slid over the fenestration template 250. That is to say, the fenestration template 250 can be inserted into the lumen 263 defined by the fenestrated stent graft 260. In some embodiments, the fenestrations 255 defined by the fenestration template 250 can be visible through the fenestrated stent graft 260. In other embodiments, the fenestration template 250 can provide a marking or indicator associated with the locations of the fenestrations 255. Thus, the fenestrations 265 can be defined along the fenestrated stent graft 260, as described above.

Although not shown in FIGS. 3 and 4, in some embodiments, a coating material can be applied and/or otherwise disposed on a surface of the fenestration template 250 configured to contact the fenestrated stent graft 260, and/or vice versa. Such a coating can, for example, allow for smooth rotation or movement of the fenestrated stent graft 265 relative to the fenestration template 250. In some embodiments, such coating material can, for example, smooth relatively small-scale roughness due to the layer-by-layer deposition of the modeling material during 3-D printing.

As shown in FIG. 4, the fenestrations 265 can be disposed along the fenestrated stent graft 260 in any suitable manner. Similarly, the fenestrations 265 can have any suitable size, diameter, and/or shapes. For example, the fenestrations 265 can have substantially the same size and/or shape as the fenestrations 255 defined by the fenestration template 250, which in turn, can correspond to the size and/or shape of the branch vessel openings and/or the adjusted or calculated branch vessel openings in the patient's aorta, as described above. For example, the fenestrations 265 can be substantially circular if the corresponding adjusted and/or calculated branch vessel is substantially circular and would otherwise be covered by the graft material when the fenestrated stent graft 260 is positioned in the patient's aorta. Similarly, the fenestrations 265 defined by the fenestrated stent graft 260 can be disposed at any suitable position along a length of the fenestrated stent graft 260. For example, in some embodiments, the fenestrations 265 can be located at and/or near the proximal end portion 261 or the distal end portion 262 of the fenestrated stent graft 260. In this embodiment, the fenestrations 265 are disposed at or near the proximal end portion 261 of the fenestrated stent graft 260. In some embodiments, the peripheral edges of the fenestrated stent graft 260 that define the fenestrations 265 can be at least partially reinforced to provide stability, for example, for anchoring of fenestrated stent graft 260 to the branch vessels extending from the aorta. In some embodiments, the peripheral edge defining a fenestration 265 can be stitched or sutured using wires and/or can be coupled (e.g., via stitches) to a ring or a similar support frame.

Figure 5:
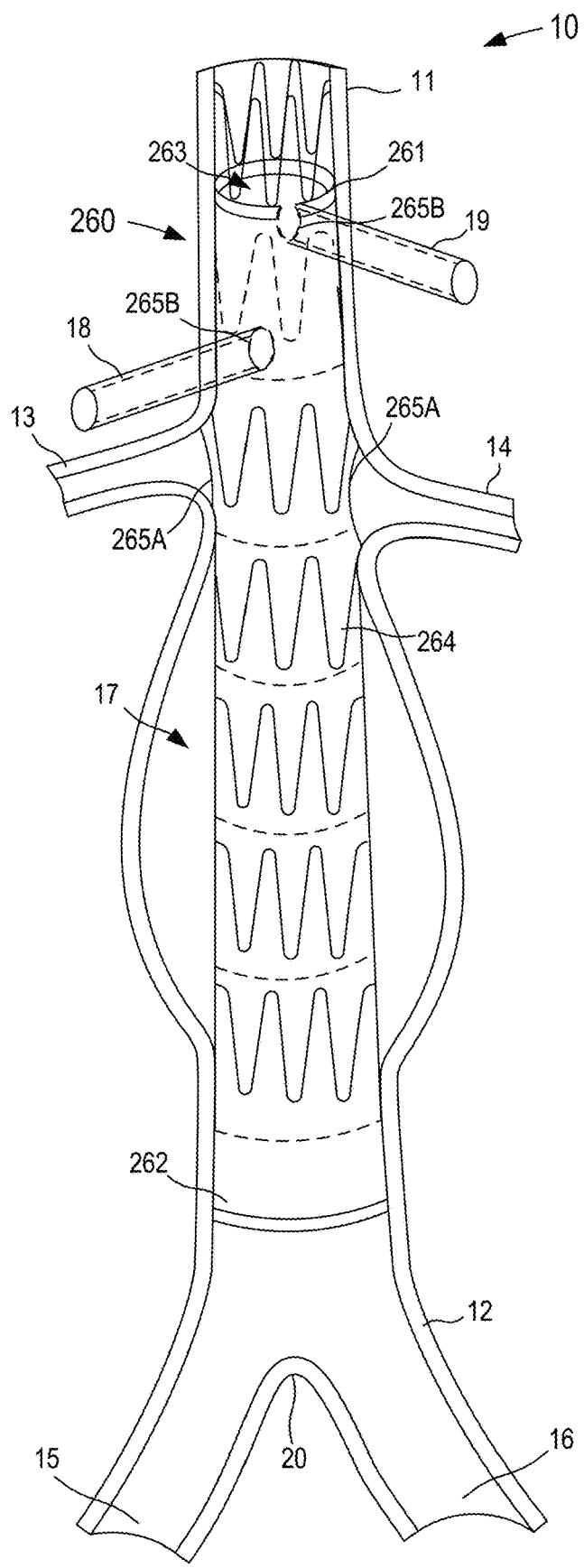
FIG. 5 is an illustration of the portion of the fenestrated stent graft of FIG. 4 positioned, for example, within a portion of a diseased abdominal aorta.

As shown in FIG. 5, when the fenestrations 265 are defined along the fenestrated stent graft 260, the fenestrated stent graft 260 can be positioned within a portion of the patient's body using any suitable endovascular procedure. In this embodiment, the fenestrated stent graft 260 is positioned within the patient's aorta 10. As shown, the fenestrated stent graft 260 can include, for example, a first set of fenestrations 265A, which are associated with and/or otherwise correspond to the left renal artery 14 and the right renal artery 13. Specifically, the fenestrations 265A are each aligned with its corresponding renal artery 13 or 14 and can each have a size, shape, and/or configuration that is associated with its corresponding renal artery 13 or 14. In some embodiments, the size, shape, and/or position of the fenestrations 265A is associated with and/or substantially corresponds to the adjusted and/or calculated size, shape, and/or position of its corresponding renal artery 13 and 14. For example, placing the fenestrated stent graft 260 within the aorta 10 can, for example, alter, shift, rotate, translate, morph, and/or otherwise reconfigured the arrangement of the patient's aorta 10. Thus, by basing the fenestration template 250 off of the updated model the size, shape, and/or position of the fenestrations 265 defined by the fenestrated stent graft 260 can correspond to the desired branch vasculature (e.g., the left renal artery 14 and/or the right renal artery 13). Moreover, in addition to positioning the fenestrated stent graft 260 within a portion of the patient's aorta 10, the renal arteries 13 and/or 14 can also be stented, for example, through the fenestrations 265A (not shown in FIG. 5). As such, the fenestrated stent graft 260 and the stents within the renal arteries 13 and/or 14 can limit and/or substantially prevent migration of the fenestrated stent graft 260 relative to the patient's aorta 10.

As shown in FIGS. 4 and 5, in some embodiments, the fenestrated stent graft 260 can include a second set of fenestrations 265B, which are associated with and/or otherwise correspond to other branch vessels that otherwise, might be blocked by an un-fenestrated portion of the fenestrated stent graft 260. For example, the fenestrations 265B can be associated with and/or otherwise correspond to the superior mesenteric artery (SMA) 18 and the celiac artery 19, respectively. In other embodiments, the fenestrated stent graft 260 can define fenestrations to accommodate more or fewer branch vessels than illustrated here. For example, in some embodiments, the fenestrated stent graft 260 can define fenestrations to accommodate the inferior mesenteric artery (IMA), internal iliac arteries, and/or the like. Thus, the fenestrations 265 defined by the fenestrated stent graft 260 can allow blood to flow from the aorta 10 to the branch vasculature, which would otherwise be obstructed by the fenestrated stent graft 260 material.

As shown in FIGS. 4 and 5, in some embodiments, the arrangement of the fenestrated stent graft 260 and/or the patient's aorta can be such that a fenestration 265 is partially defined by the fenestrated stent graft 260. For example, as shown, the proximal most fenestration 265B is disposed at the proximal end of the fenestrated stent graft 260 and corresponds to the celiac artery 19 that is partially covered by the graft material during deployment. As such, the fenestration 265B for the celiac artery 19 is partially circular or U-shaped to accommodate the portion of the celiac artery 19 otherwise blocked by the graft material. In other embodiments, any of the fenestrations 265 can have non-circular and/or irregular shapes.

In some embodiments, the fenestrations 265 can be marked to facilitate location of the fenestrations 265 during deployment of the fenestrated stent graft 260. For example, the peripheral edges of the fenestrated stent graft 260 that define the fenestrations 265 may be sutured using gold wires and/or wires of other radio-opaque materials. Similarly, the location of the fenestration 265 can be marked by one or more radio-opaque markers 212. Such radio-opaque wires or markers can facilitate fluoroscopic visualization of the fenestrations 265 during an endovascular repair procedure and allow a physician to locate the fenestration 265 with respect to the corresponding branch vessel. In other embodiments, the fenestrations can be sutured and/or otherwise marked using any suitable material that can increase visibility, for example, when using any suitable imaging device (e.g., MRI scan, CAT scan, PET scan, X-Ray scan, ultrasound, etc.).

As described above, the fenestrated stent graft 260 can have an arrangement that substantially corresponds with the fenestrated template 250. Moreover, the fenestrated template 250 can be, for example, 3-D printed and/or otherwise output by the output device 210 based on an adjusted, updated, calculated, and/or otherwise modified model of the patient's aorta 10. When the fenestrated stent graft 260 is inserted into the patient's aorta 20, the arrangement of the aorta 10 shifts and/or otherwise moves in response thereto. Thus, with the fenestrated stent graft 260 being based on the fenestrated template 250, which in turn, is based on the updated model representing the shifted and/or moved arrangement of the patient's aorta 10, the fenestrations 265 each can be accurately sized, shaped, and/or positioned to correspond with its associated branch vasculature, as described in detail above.

Figure 6:
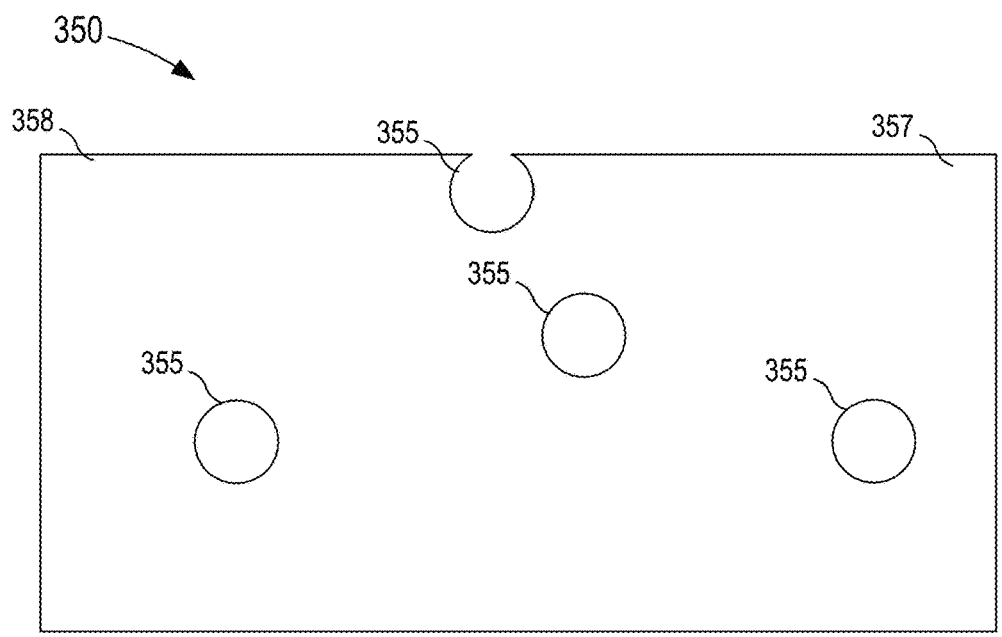
FIG. 6 and FIG. 7 are illustrations of at least a portion of a fenestration template according to another embodiment, in a first configuration and a second configuration, respectively.
Figure 7:
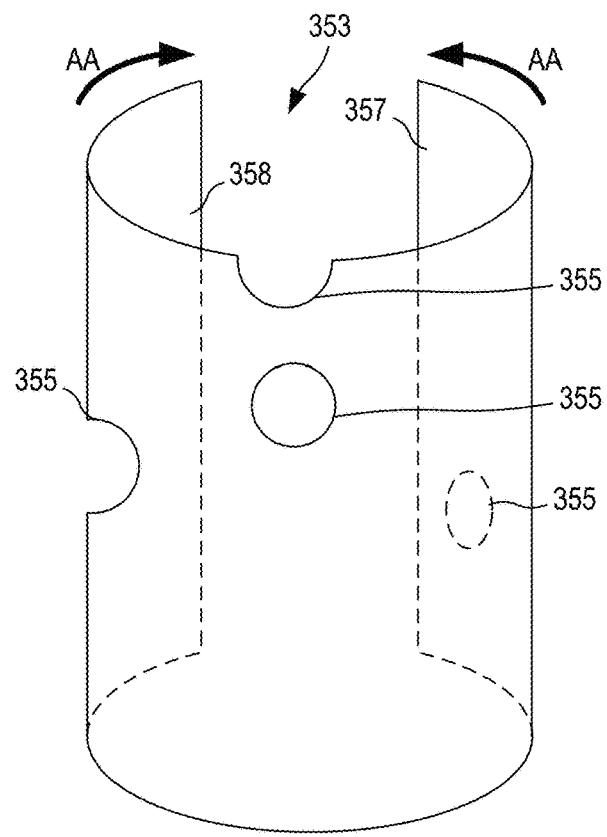

While the fenestration template 250 is shown and described above as being 3-D printed and/or otherwise produced by a rapid prototyping machine to have a substantially cylindrical shape, in other embodiments, a fenestration template can be, for example, substantially flat and configured to be rearranged to form desired fenestration template. For example, FIGS. 6 and 7 illustrate a fenestration template 350 according to another embodiment, in a first configuration and a second configuration, respectively. As shown in FIG. 6, in this embodiment, the fenestration template 350 is a substantially flat sheet with fenestrations 355 corresponding to the openings of branch vessels of the aorta (e.g., the aorta 10 in FIG. 1). As described above with reference to the fenestration template 250, the fenestration template 350 can be manufactured using any suitable process such as three-dimensional (3-D) printing or additive prototyping/manufacturing, subtractive manufacturing, 3-D printing, and/or the like or a combination thereof. As such, the fenestration template 350 can be configured to substantially correspond to an updated and/or adjusted model of the patient's aorta, as described in detail above.

In some embodiments, the fenestration template 350 can be made of any elastic material such as thermoplastic, plaster, metal alloy, titanium alloy, paper, metal foil, plastic film, photopolymer, a biocompatible graft material, and/or any other suitable material. In this manner, the fenestration template 350, for example, can be manipulated from its first configuration, in which the fenestration template 350 is a substantially flat sheet, to its second configuration, in which the fenestration template 350 at least partially forms a tubular and/or cylindrical shape, as indicated by the arrows AA in FIG. 7. For example, in some embodiments, the fenestration template 350 can be manipulated to form a partial tubular or cylindrical structure. In such embodiments, the fenestration template 350 can be formed from a substantially resilient material that can, for example, maintain its shape until a sufficient force is exerted to reconfigure the fenestration template 350. In this manner, the fenestration member 350 can be positioned relative to a stent graft or the like (e.g., the fenestrated stent graft 160 in FIGS. 4 and 5) and reconfigured to be placed in contact with an inner surface or an outer surface of the stent graft.

In other embodiments, the fenestration template 350 can be reconfigured to form a substantially complete tubular or cylindrical structure. For example, a first end portion 357 of the fenestration template 350 can be configured to overlap and couple to a second end portion 358 of the fenestration template 350. In some embodiments, the first end portion 357 and the second end portion 358 can include a coating, an adhesive, and/or the like configured to couple the first end portion 357 to the second end portion 358. In some embodiments, the first end portion 357 and/or the second end portion 358 can include indicia and/or other indicator configured to indicate, for example, a diameter of the fenestration template 350 when placed in the second configuration. Thus, the fenestration template 350 can be sized to fit a given stent graft and/or lumen of the aorta.

As described in detail above, the fenestration template 350 defines a set of fenestrations 355 that can be disposed along the fenestration template 350 at a position associated with an opening to a corresponding branch vasculature of the aorta. The size, shape, and/or configuration of the fenestrations 355 similarly can be associated with the openings of the branch vasculature. More specifically, the arrangement of the fenestrations 355 can substantially correspond to an adjusted, calculated, updated, and/or otherwise modified arrangement of the patient's aorta in response to the placement of an endovascular stent graft. In this manner, the fenestration template 350 can be transitioned to its second configuration and placed in engagement with an endovascular stent graft to facilitate, mark, locate, and/or otherwise at least partially define a set of fenestrations in the endovascular stent graft that substantially correspond to the modified arrangement of the patient's aorta. As described in detail above, with the desired fenestrations defined by the stent graft, the stent graft can be positioned within the patient's aorta (see e.g., FIG. 5) during any suitable endovascular procedure.

While the fenestration templates 250 and 350 are shown and described above as defining the fenestrations 255 and 355, respectively, in other embodiments, a fenestration template can include one or more bumps and/or protruding structures instead of or in addition to fenestrations or markings to designate the locations of the fenestrations on the stent graft. The protruding structure may be used to mark and/or cut the graft material to define the fenestrations therein. In some embodiments, such a fenestration template can include one or more protruding structures on the outer surface or on the inner surface of the fenestration template according to what surface is configured to contact the stent graft. The protruding structures can be of any suitable dimension and/or shapes. For example, the protruding structure can have a semi-spherical shape or a conical shape, and/or can have or form a pointed tip. As such, the protruding structures can be configured to mark locations of the fenestrations on the stent graft material upon contact using, for example, a thermal, mechanical, chemical device and/or reaction. For example, the protruding structures may be heated (e.g., electrically) to act as thermal cautery tools for generating fenestrations in the graft material. In other embodiments, the protruding structures may have sharp tips used to puncture the graft material to form the fenestrations therein.

Figure 8:
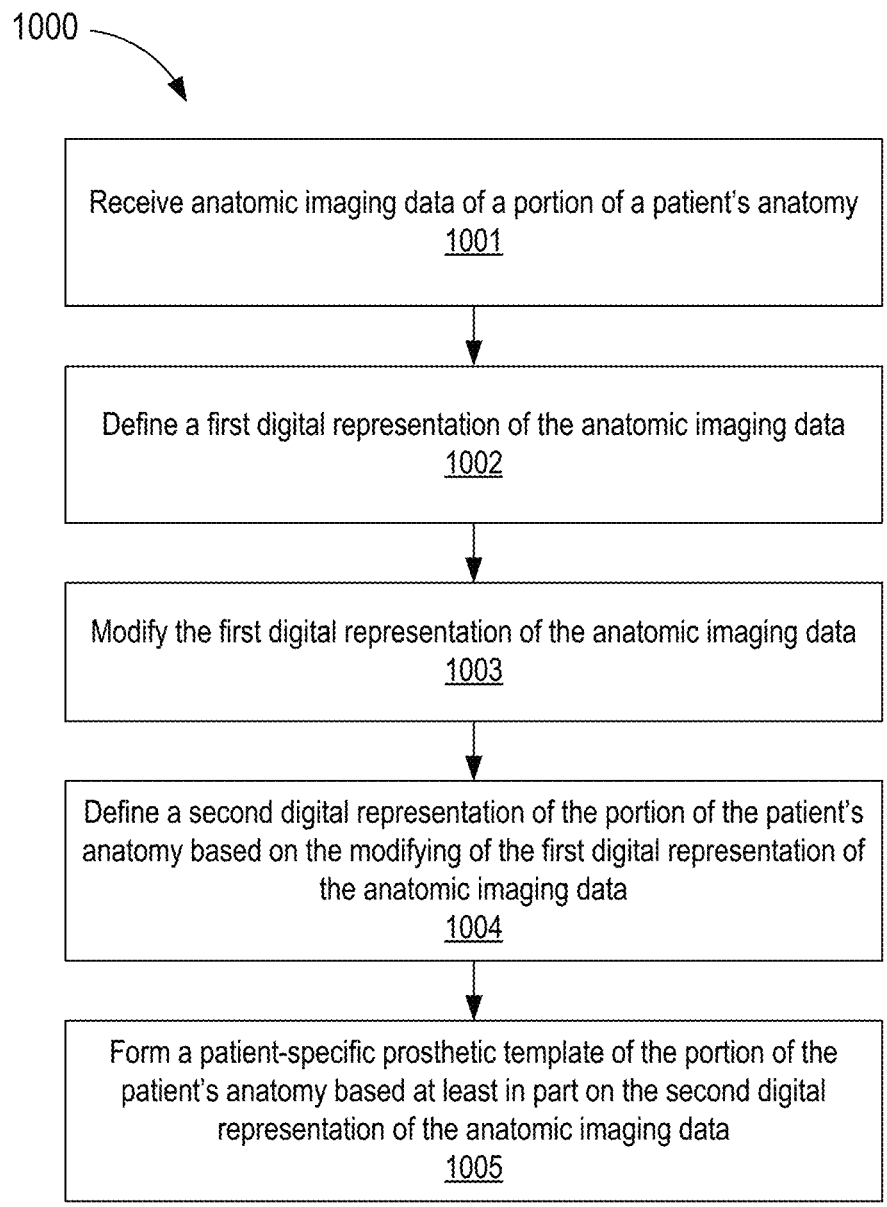
FIG. 8 is a flowchart illustrating a method of forming a prosthetic, such as a stent graft, according to an embodiment.

Referring now to FIG. 8, a flowchart is presented illustrating a method 1000 of forming a patient-specific prosthetic (e.g., an aortic stent graft) according to an embodiment. The method 1000 includes receiving anatomic imaging data of a portion of a patient's anatomy (e.g., including a blood vessel, such as an abdominal aorta, and/or associated branch blood vessels), at 1001. In some embodiments, an electronic device such as a PC or workstation receives the anatomic imaging data. The electronic device can include a graphic user interface-driven application. The imaging data is from an imaging device in communication with the host device such as, for example, an X-ray device, a computed tomography (CT) device, computed axial tomography (CAT) device) a magnetic resonance imaging device (MRI), a magnetic resonance angiograph (MRA) device, a positron emission tomography (PET) device, a single photon emission computed tomography (SPECT) device, an ultrasound device, and/or any other suitable device for imaging a portion of a patient and/or a combination thereof (e.g., CT/MRA device, PET/CT device, SPECT/CT device, etc.). In some embodiments, the imaging device can scan and/or otherwise capture imaging data of the patient's abdominal aorta and/or a portion thereof.

More specifically, the anatomic imaging data of the portion of the patient's anatomy can be loaded as an input. For example, a user can select and load a DICOM contrast CT series of the patient abdomen. In some embodiments, a variety of images can be loaded, including, for example, computed tomography (CT) images, magnetic resonance (MR) images, and ultrasound (US) images. In some embodiments, two or more images of the same image type or of different image types can be fused to improve image quality, simplify segmentation, and improve measurement accuracy. For example, in some embodiments, different image types (e.g., MR and CT) can be geometrically registered to improve segmentation. Additionally, some features of the portion of the patient's anatomy may be more clearly visible in one image type than another, so fusion of the information from two or more images can improve the clarity and accuracy of the images and/or data.

In some embodiments, data can be resampled for improved image resolution. Data interpolation can be used to improve measurement accuracy. For example, if images are sampled 2 mm apart along the Z-axis, then the point-to-point distance between two images can only be measured in steps of 2 mm. By interpolating between the images (i.e., creating intermediate images between the two), measurement accuracy can be improved. As another example, an additional CT image can be created from two CT images spaced 2 mm apart, such that the additional CT image is placed between the original two CT images and spaced only 1 mm from each of the first two CT images. Data interpolation can improve the accuracy of measurements to, for example, sub-pixel accuracy.

A first digital representation of the anatomic imaging data is defined, at 1002. For example, the electronic device can define the first digital representation or the like associated with and/or corresponding to the patient's anatomy. The first digital representation can be, for example, an anatomic model of the patient's abdominal aorta. In some instances, the first digital representation can be an anatomic model of the patient's abdominal aorta, a first branch blood vessel, and a second branch blood vessel based on the anatomic imaging data. Moreover, in some instances, a user can manipulate the electronic device to cause the anatomic model to be graphically presented on a screen using, for example, a solid modeling program and/or any other computer-aided design (CAD) program.

The images associated with the anatomic imaging data can be displayed such that the user can better visualize the patient's anatomy. The images can be displayed in a standard layout for 3-D medical images. For example, the images can be displayed in a 2×2 layout as axial, sagittal, and coronal slices. The images can also be displayed in a 3-D cube view. In some embodiments, the user can manipulate the images for improved visualization of the anatomy. For example, the user can step through the slices, change contrast settings, and change the zoom settings (i.e., adjust the magnification).

Image processing algorithms can be used to segment the portion of the patient's anatomy (e.g., the aorta) to focus on the volume of interest. After segmentation, the image data can be cropped to speed up image processing. In some embodiments, the volume of interest can be manually entered by a user via a user-selected file or through interactive user input. In other embodiments, the volume of interest can be determined automatically using image analysis techniques. For example, the aorta can be identified in contrast CT images. Image analysis techniques can then be used to automatically detect a particular portion of the aorta, such as the space ranging from the celiac artery to the renal artery to the ileac arteries.

In some embodiments, the image processing methods (i.e., image analysis techniques) can determine a sub-volume of interest for further processing. For example, brightness and/or edge detection can be used to determine the location of a particular portion of a patient's anatomy, such as the location of the abdominal aorta and branch vessels (e.g., the renal artery). The location data of the sub-volume of interest can be used to define the sub-volume of interest such that it contains only the data associated with the sub-volume of interest (e.g., a sub-volume of interest including only the aorta and branch vessels).

In some embodiments, atlas-based methods can be used to model the anatomy to avoid noisy or incomplete data. Such methods begin with the expected layout of the patient's anatomy, such as the relative locations of anatomical features and expected ranges of dimensions. For example, for a typical patient, the celiac artery is expected to be positioned above the renal arties. Additionally, the diameters of the renal arteries are expected to range from about 4 mm to about 10 mm.

In some embodiments, the method can include modifying the initial anatomical model (i.e., the first digital representation) created from the anatomic imaging data using additional data collected through any method described herein. Because the initial anatomical model is used as a starting point and the initial anatomical model is then adjusted with collected data, this method avoids holes in the model that can result from incomplete data. Additionally, noise can be avoided because a user or image processing algorithm can recognize if collected data is within an expected range of the initial anatomical model. If collected data is outside of an expected range, the data can be discarded or flagged for review.

In some embodiments, a combination of user input and automatic detection is used to define the volume of interest. For example, after an initial automatic detection using the methods described herein, user input can be used to refine the boundaries of the volume of interest.

Particular portions of the patient's anatomy, such as the branch vessels of the aorta, can be automatically segmented. In some embodiments, segmentation can be through "region growing." For "region growing" segmentation, initial seed points can be user-specified or automatically detected. Next, additional nearby data points with similar characteristics to the initial seed points can be identified. Similar characteristics can include, for example, intensity values. For example, CT images can be quantified using Hounsfield units. An expected range of Hounsfield units for blood vessels in contrast CT images can be identified. The expected range can be used to identify data points in the CT images that are likely to be associated with blood vessels. The initial seed points and nearby data points with similar characteristics can be combined to create a model of the particular portion of the patient's anatomy, such as the branch vessels. In other embodiments, the particular portion of the patient's anatomy can be automatically segmented using deformable models. For example, the boundary of a vessel can be detected in a first image. The boundary can be, for example, circular or elliptical. The boundary in the first image can be "grown" through the volume of interest (i.e., the boundary shape in the first image can be stacked through the volume). Constraints can be imposed on the overall shape of the "grown" boundary such as, for example, smoothness or orientation. In other embodiments, an atlas-based model can be used to segment the vessel. An initial "atlas" model can be constructed from training data and expert knowledge. Additional data, which may be collected from the patient, can be used to map the initial "atlas" model to the patient's anatomy.

Following segmentation, portions of the patient's anatomy can be extracted from the segmented images. For example, the aortic trunk and the branch vessels can be segmented and extracted. Morphological filters can be used to separately extract the aortic trunk and branch vessels. Alternatively or additionally, in some embodiments, elliptical contours can be fitted to the segmented surface points. Outlier detection methods can then be used to exclude branch vessel points and only fit points that belong to the main trunk.

In some embodiments, each vessel can be identified using a user's knowledge of anatomy and patient orientation (e.g., right versus left). For example, the user can distinguish between the left and right renal arteries and between the celiac artery and the superior mesenteric artery (SMA). Another example is that the user may know the relative locations of vessels in a typical anatomy (e.g., the celiac is above the renal arteries) and the user can use this information in identifying each vessel. A third example is that the user may intend to identify a portion of the aorta with a specific shape (e.g., a long tube with four to six branch vessels). Each of the dimensions of the specific shape can have an expected range of values (e.g., the aorta diameter will be between 15 mm and 30 mm). Thus, knowledge of the anatomy can assist with segmentation and locating, for example, an aneurysm. Additionally, relevant information from the patient's medical record (e.g., a missing renal artery) can be used.

In some embodiments, centerlines of portions of a patient's anatomy can be extracted from the segmented portions. For example, the centerlines of the aortic trunk and branch vessels (i.e. the lines passing through the central axes of the aortic trunk and branch vessels and following the geometry of the main trunk and branch vessels) can be extracted from the segmented portions of the aortic trunk and branch vessels. In some embodiments, the centerlines can be extracted automatically. In some embodiments, a curved planar reformation (CPR) image can be optionally generated and displayed. In some embodiments, a distance transform can be applied to a segmented image and can connect points with maximum distances using a fast marching method. The distance transform allows for distances from each point in the segmented image to the closest neighbor of each point in the background to be computed. For example, if the distance transform is applied to a circular contour the distances will be maximum at the center and decrease radially. A fast marching method can then be applied to connect points with maximum distances. In other embodiments, contours (e.g., elliptical, spline, etc.) can be fit to the segmented image and centroids or weighted centroids of the contours can be computed to define the centerline. In other embodiments, vessel specific properties can be computed and used to compute centerlines. For example, vesselness, a measure of how similar a structure is to tube used in some methods of image segmentation, can be computed and used to compute centerlines.

The first digital representation of the anatomic imaging data is modified, at 1003. For example, as described above, the patient's anatomy can shift, rearrange, and/or otherwise adjust when a prosthetic such as an endovascular stent graft is disposed therein. When the portion of the patient's anatomy is a portion of the abdominal aorta, this shifting can result in a corresponding shifting or movement of the openings to the branch vasculature in fluid communication with the aorta, which in turn, can result in a reduction in accuracy of the first digital representation of the anatomic imaging data relative to the shifted anatomy. Accordingly, in some embodiments, the electronic device can adjust and/or update data associated with the first digital representation. For example, the data can be adjusted and/or updated based on patient data such as a degree of aortic angulation at the juxtarenal neck or other segment of the aorta; a degree, pattern, and location of atherosclerotic disease including plaque, calcification, and/or thrombus; morphometric characteristics of the vascular structure that influence size, position, angulation, or tortuosity such as vessel diameter (i.e., vascular lumen diameter); and/or vessel wall thickness, vessel length, location and number of branch arteries, and/or the like; anthropomorphic data of the patient such as body composition, body temperature, height, weight, BMI, abdominal circumference (absolute or normalized), age, and/or the like; pre-existing vascular or extravascular prostheses or foreign bodies, and/or the like. In some instances, the data can be adjusted and/or updated based on data associated with mechanical properties of the prosthesis such as, for example, body material or fabric type, stent or support strut geometry and/or thickness, type of metals or other support materials, stiffness and diameter of the prosthesis, an amount of oversizing of the prosthesis, and/or the like. In addition, the data can be adjusted and/or updated based on data associated with a delivery method of the prosthesis such as, for example, an impact of specific delivery methods such as use of guide wires, catheters, and/or the like. A second digital representation of the portion of the patient's anatomy is defined based on the modifying of the first digital representation of the anatomic imaging data, at 1004. In other words, the first digital representation of anatomic imaging data can be associated with a portion of the patient's anatomy in a first configuration and a second digital representation of the anatomic imaging data can be associated with the portion of the patient's anatomy in a second configuration. The portion of the patient's anatomy can transition from the first configuration to the second configuration in response to insertion of a prosthetic (e.g. a patient-specific prosthetic).

In some embodiments, the first digital representation of anatomic imaging data can be modified based on a predetermined data set, and the predetermined data set can be based on data associated with the second digital representation. By quantifying characteristics of, for example, a patient-specific prosthetic, a patient, and/or a manner of introducing the patient-specific prosthetic to a portion of a patient's anatomy, the data associated with the first digital representation can be adjusted and/or updated to define the second digital representation based on an anticipated, predicted, predetermined, calculated, and/or otherwise probable shift in the arrangement resulting from the insertion and indwelling of a prosthetic (e.g., an endovascular stent graft). Said another way, the first digital representation can be based on a predetermined data set, and the predetermined data set can be updated based on data associated with an anticipated, predicted, predetermined, calculated, and/or otherwise probable shift in the arrangement resulting from the insertion and indwelling of the prosthetic.

In some embodiments, the anatomic imaging data can be a first anatomic imaging data set. The modifying of the first digital representation of the first anatomic imaging data set can be based on data associated with the patient-specific prosthetic, a patient, and/or a manner of introducing the patient-specific prosthetic to a portion of a patient's anatomy. The data associated with the patient-specific prosthetic, a patient, and/or a manner of introducing the patient-specific prosthetic to a portion of a patient's anatomy can be updated with data associated with a second anatomic imaging data set, the second anatomic imaging data set being representative of the patient-specific prosthetic disposed within the portion of the patient's anatomy.

Specifically, in some embodiments, the modification of the first digital representation to define a second digital representation of the portion of the patient's anatomy (i.e. the predicted changes in the patient's anatomy) can be based on predicted changes to the centerline of a portion of the patient's anatomy. For example, the modification can be based on predicted changes to the extracted centerline of the aortic trunk. The extracted centerline (as described above) is typically a sequence of points in 3-D space (e.g., having x-, y-, and z-coordinates). A low order polynomial function can be fitted to the points using a least squares fitting technique to produce a modified centerline (i.e., an adjusted centerline) that is a prediction of the shape of the portion of the patient's anatomy after insertion of a graft.

In some embodiments, the modification of the first digital representation to define a second digital representation of the portion of the patient's anatomy (i.e. the predicted changes in the patient's anatomy) can be based on the expected deformation of the patient's anatomy as a result of inserting a device (e.g., a graft) into the anatomy. For example, mathematical models of the segmented volumes and/or surfaces, such as finite element method (FEM) or parametric representations, can be created based on expected deformation of the segmented volumes and/or surfaces. Models reflecting the expected deformation can be built from training data consisting of pre-procedure, intra-procedure, and post-procedure images. The anatomy of interest can be segmented and the resulting changes can be modeled using machine learning approaches. In other words, data can be collected from a deformed portion of one or more patients' anatomy (e.g., a deformed aorta) and the data can be used to create a training data set. The training data set can be used to model the predicted deformation of a portion of a patient's anatomy in future procedures.

In some embodiments, the modification of the first digital representation to define a second digital representation of the portion of the patient's anatomy can take into account characteristics of a particular device (e.g., a patient-specific prosthetic) to be delivered to the anatomy. For example, the modification can take into account the wire stiffness of a graft and account for variations in wire stiffness between manufacturers. In some embodiments, for example, a lower order polynomial fit can be used to model the predicted change in centerline if a stiffer device is inserted into the anatomy (e.g. a stiffer graft). Additionally, training data can be used to model changes as a result of the characteristics of particular devices.

In some embodiments, the modification of the first digital representation to define a second digital representation can take into account anatomic-specific information (e.g., characteristics associated with a specific patient or set of patients). For example, if the particular patient's anatomy is unusually angulated, the anatomical shift of the anatomy as a result of a device being inserted (e.g., a graft) is likely to favor one side of the anatomy (e.g. the aorta vessel wall). Additionally, the insertion location (e.g., left versus right femoral artery) can cause the device to favor one side of the anatomy (e.g. aorta vessel wall). Training data can also be used to model changes as a result of a particular patient's anatomy. Additionally, in some embodiments, the modification of the first digital representation to define a second digital representation can take into account procedure-specific details (i.e., characteristics associated with a method of introducing a patient-specific prosthetic to the anatomy). For example, the modification can account for insertion location (e.g., left side versus right side), patient breathing, and/or physician preferences.

In some embodiments, the user (e.g., clinician or surgeon) can manually account for patient-specific details (i.e., characteristics associated with a patient). For example, a user can use a different method to locate (for digitally representation) the distal or proximal end of a vessel depending on the presence of a calcium deposit. In other embodiments, the modification of the first digital representation can take into account patient-specific details using algorithms. For example, the modification can account for calcium deposits or plaque, the presence of artifacts obstructing blood flow through the aorta, and/or the angle of curvature of the aorta and branch vessels.

In some embodiments, intra-procedure data can be incorporated to refine algorithms used to modify the first digital representation. The intra-procedure data can include imaging data such as fluoroscopy, CT, or any other suitable imaging data. Additionally, in some embodiments, machine learning can be used to refine the algorithms. In some embodiments, intra-procedural data can be used to validate measurements and refine the algorithms. A model (e.g., a modified digital representation) can first be used to predict changes in the anatomy or how the graft would line up along the centerlines of the anatomy. The intra-procedure data can then be analyzed to observe the actual changes. The deviations from the predicted changes to the actual changes (obtained from intra-procedure data) can in turn be used to refine future models (e.g., future digital representations).

For example, patient breathing can deform organs in a non-rigid manner. To account for non-rigid movements, a non-rigid deformation can be applied to pre-operative models (e.g., a first digital representation). The amount and shape of deformation resulting from a force on a graft caused by patient breathing. Intra-procedure images of a patient can be analyzed and compared to the patient's pre-operative images to determine the appropriate non-rigid deformation for future digital representations.

As another example, intra-procedure images can be used to modify the first representation (i.e. to build a predictive model) based on where the device (e.g. a graft) is expected to eventually be located in the patient based on the side of insertion. For example, grafts that are inserted from the right side of a patient may typically shift to a positon next to the left side of the aorta wall. The expected location can be quantified through intra-operative measurements and a predictive model can be created.

Calcium deposits along the arterial wall of a vessel can affect the stiffness of the vessel. Additionally, other calcium deposits and/or diseased portions of the vessel can increase or decrease the stiffness of the arterial wall. Stiffness of the vessel wall is inversely related to the amount of flexibility of the vessel wall. In some embodiments, calcium deposits and/or diseased portions can be accounted for during the modification of the first digital representation pre-operatively by modeling the stiffness as a material property. For example, finite element models can be used that model the stiffness as a material property.

When calcium deposits are located near branch vessels, identification of the location of the branch vessels can be more difficult. In some embodiments, expert clinician knowledge regarding the location of calcium deposits and/or branch vessels can be incorporated into the modification of the first digital representation to define a second digital representation. Clinician inputs can be collected and used to modify the first digital representation (i.e., built into a predictive model) that can be applied to future patients and/or procedures. As the number of patients in a training set increases, the accuracy of the predictive model can increase. Additionally, as more data is collected via the training set, outlier patient data can be discarded.

In some embodiments, portions of the first digital representation can be modified to define the second digital representation using a centerline modified for the second digital representation as described above (i.e. an adjusted centerline). For example, the branch vessel locations (i.e., expected locations of the branch vessels during the procedure) can be predicted using the adjusted centerline of an aorta. As described above, the adjusted centerline can be used to predict the path that the graft will take within a patient's anatomy. The adjusted branch vessel locations can then be predicted by projecting the vessel endpoints (i.e., the points where the vessels join the aorta which can be obtained from imaging data) on to the adjusted centerline of the aorta. Identification of the branch vessel endpoints (proximal and distal ends) can be performed automatically or manually. To identify the branch vessel endpoints automatically, a segmented vessel surface and a segmented aorta surface can be produced using the segmentation steps described above. The intersection points of the segmented vessel surface and the segmented aorta surface can then be used to locate and define the branch vessel endpoints (i.e., where the branch vessel connects to the aorta).

In other embodiments, vessel locations can be predicted by projecting a central point of the vessel along the adjusted centerline of the aorta. The identification of the central point of the branch vessels can be performed automatically or manually. To identify the central point of the branch vessel automatically, the centerlines for the branch vessels, the main centerline of the aorta, and the segmented aorta produced by the segmentation steps above can be used to determine the junction point (also referred to as the "branch vessel junction") where a branch vessel centerline and an outer surface or wall of the segmented aorta intersect (i.e. the central point of the vessel along the outer surface of the aorta based on the adjusted centerline of the aorta). The vessel radius can then be estimated and the vessel location can be defined as ±the radius from the projected branch vessel junction (i.e. the vessel central point on the outer surface of the segmented aorta).

In some embodiments, pre-operative images can be deformed (i.e. the first digital representation can be modified to define the second digital representation) using a deformation field. The deformation field can be created using the output from the finite element models described above for deforming the aorta and associated branch vessels. The output from the finite element models is a deformation field with x, y, and z displacement values for every voxel in the 3-D image. The deformation field can then be applied to pre-operative images to deform them the images will reflect the predicted change in shape of the patient's anatomy as a result of device insertion. Thus, a user (e.g. a clinician or a surgeon) can use the deformed images in accounting for deformations during pre-procedure planning. Additionally, the deformed images can be used as a training tool for surgical residents to aid in learning about intra-operative changes to the shape of the aorta, centerline adjustment, and the like.

In some embodiments, centerlines (e.g., centerlines of the aortic trunk and branch vessels) can be extracted automatically from mathematical models. Said another way, centerlines can be extracted (using methods described herein) from deformed images. In such embodiments, centerlines can be extracted from intra-procedure or post-procedure image data reflecting anatomy deformed by device insertion. Branch vessel locations can then be predicted based on the extracted centerlines. Similarly as described above, these centerlines can be used for pre-procedure planning (e.g. modification of the first digital representation to define a second digital representation) and for training/teaching aids.

A patient-specific prosthetic template of the portion of the patient's anatomy is formed based, at least in part, on the second digital representation of the anatomic imaging data, at 1005. For example, as described above, the electronic device can include and/or can send a signal to an output device such as a 3-D printer or a rapid prototyping machine. As such, the output device can be caused to output the patient-specific prosthetic template associated with the updated, adjusted, calculated, and/or otherwise modified data, which in turn, is associated with a projected (i.e., predicted), anticipated, and/or calculated arrangement of the patient's abdominal aorta. The patient-specific prosthetic template can include openings (fenestrations), protrusions, markers, indicators, frangible portions, and/or any other suitable feature corresponding to, for example, the openings of the aorta leading to the branch vasculature, as described above with reference to, for example, the fenestration template 250 and the fenestrated stent graft 260. For example, the patient-specific prosthetic template (also referred to as a "patient-specific fenestration template") can include a first indicator or marker corresponding to the location of a first branch blood vessel extending from a patient's aorta in the second digital representation and a second indicator or marker corresponding to the location of a second branch blood vessel extending from a patient's aorta in the second digital representation. The first marker and the second marker can be a first opening and a second opening in the patient-specific prosthetic template.

For example, in some embodiments, the relative locations of the vessels can be automatically quantified in a 3-D or 4-D coordinate system. Additionally, relevant dimensions such as, for example, diameters and volume of flow, can be automatically quantified. This information can be used to modify the first digital representation to define the second digital representation of the portion of the patient's anatomy. The second digital representation can then be used to create a fenestration template (also referred to as a "patient-specific prosthetic template"). The fenestration template can be used to modify a graft. For example, the fenestration template can be used to create fenestrations in a graft at the predicted location of the vessels such that fenestrations are at the appropriate location and of an appropriate size and shape to allow pass-through of the vessels. In some embodiments, for example, the fenestration template can be a flat sheet configured to be wrapped around a portion of an aortic graft to allow a used to identify fenestration locations in the aortic graft. In embodiments in which the fenestration template includes a first marker and a second marker, a first fenestration location in the aortic graft can correspond to the first marker and a second fenestration location in the aortic graft can correspond to the second marker. In some embodiments, the fenestration template can include a tubular body defining a lumen configured to be at least partially disposed over and aortic graft. In other embodiments, the fenestration template can include a tubular body configured to be at least partially disposed in a lumen of an aortic graft. Alternatively, in some embodiments, the digital representation data can directly feed into the graft manufacturing process to produce a fenestrated graft.

For example, in some embodiments, to form a fenestration template of a portion of a patient's aorta, the average diameter of the aorta at user-specified end points at the celiac and SMA branch vessels can be computed. Next, the locations of the branch vessels can be translated to cylindrical coordinates on the surface of a cylinder. The cylinder can have a diameter equal to the average diameter of the aorta (e.g., the average of the diameter at the celiac and the SMA branch vessels). Each branch vessel location can be defined by its central point and radius on the surface of this cylinder as described above.

In some embodiments, clinical knowledge can be incorporated into the process of quantifying the relative location of vessels. Clinical knowledge can be incorporated automatically or manually. For example, information regarding when to block an accessory vessel, when to create a larger fenestration for multiple vessels, how to account for stenosis, visible calcium buildup, and the like, can be used to modify the template based on the second digital representation. In some embodiments, for example, an option can be provided to allow the user to either create a fenestration in the template for an accessory renal artery or to block off the accessory renal artery and not provide access through the graft in that location.

In some embodiments, a template representation (a patient-specific prosthetic template) of the vessels can be created. The template representation can be used, for example, with a 3-D printer or fed into a graft manufacturing process such as, for example, an STL model or other CAD models. In some embodiments, the template representation can be an STL model of a cylindrical shell having a wall thickness of 2 mm with fenestrations (i.e., holes) corresponding to the branch vessels. Additionally, in some embodiments, an internal serial number can be placed at the bottom of the STL model. Graft manufacturer data, such as CAD models and strut patterns, can be incorporated into the template representation. For example, manufacturer strut pattern information can be used to define fenestrations in locations on a graft without struts. In some embodiments, the graft manufacturing process can be modified such that the strut patterns are customized to not overlap with fenestration locations.

In some instances, the patient-specific prosthetic template can be used to form the patient-specific prosthetic. For example, in some embodiments, the patient-specific prosthetic can be, for example, a stent graft. In such embodiments, the stent graft and the patient-specific template can be placed in contact and/or otherwise made to engage each other. As such, the patient-specific template can be used to form at least a portion of the stent graft (i.e., the patient-specific prosthetic). More specifically, the patient-specific template can define a set of fenestrations (i.e., lumens) in a wall of the patient-specific template associated with the openings of the branch vessels of the aorta. In this manner, the patient-specific template can be used to guide the placement of and/or otherwise locate a corresponding set of fenestrations in the stent graft, each of which corresponds to an opening of a different branch vessel. In some embodiments, the patient-specific template can direct a means of defining the fenestrations (e.g., a blade, a laser, a water jet, a punch, a drill, and/or the like). In other embodiments, the patient-specific template can be configured to at least partially form the fenestrations of the stent graft (e.g., the patient-specific template can include a protrusion or the like configured to puncture and/or otherwise define an opening in the stent graft. Thus, the patient-specific template can facilitate the formation of the fenestrations defined by the stent graft, which are each disposed along the stent graft in a position corresponding to a modified and/or shifted position of a branch vessel of the aorta, which results from the placement of the stent graft, as described in detail above with reference to the fenestration patient-specific template 250 and the fenestrated stent graft 260.

Some of the embodiments described herein are configured to define a first digital representation of anatomic imaging data of a portion of a patient's anatomy and to modify the first digital representation to define a second digital representation of the portion of the patient's anatomy based on a set of characteristics associated with the patient, a prosthetic, and/or a manner of delivering the prosthetic. In other embodiments, the second digital representation of the portion of the patient's anatomy can be from a plurality of digital representations of the portion of patient's anatomy. That is to say, in some embodiments, the modifying of the first digital representation of the portion of the patient's anatomy can result in a plurality of modified digital representations of the portion of the patient's anatomy (including the second digital representation). In such instances, each modified digital representation of the portion of the patient's anatomy (simply referred to herein as "modified representation") can be based on a different set of characteristics or a different combination of the characteristics associated with the patient, the prosthetic, and/or the manner of delivering the prosthetic.

For example, a first digital representation of a portion of a patient's anatomy can be modified to define a second digital representation of the portion of the patient's anatomy based on patient data, prosthetic data, and/or a first method of delivering the prosthetic. Similarly, the first digital representation of the portion of the patient's anatomy can be modified to define a third digital representation of the portion of the patient's anatomy based on the patient data, the prosthetic data, and/or a second method of delivering the prosthetic. In this manner, a patient-specific prosthetic template such as the fenestration templates 150, 250, and/or 350 based on the second digital representation can also be specific to the first method of delivering the prosthetic, while a patient-specific prosthetic template based on the third digital representation can also be specific to the second method of delivering the prosthetic. In a similar manner, a digital representation can also be based on the size, shape, and/or configuration of the prosthetic. As such, a user can input a selection or the like of a digital representation of a specific prosthetic template from a plurality of specific prosthetic templates. Moreover, in some instances, a score, confidence value, rating, and/or any other indicator can be associated with the digital representation of each prosthetic template and can be indicative of an accuracy of the digital representation of each prosthetic template and the associated modified representation of the patient's anatomy. Said another way, a digital representation of a plurality of patient-specific prosthetic templates and a plurality of confidence values can be defined. Each confidence value from the plurality of confidence values can be associated with the digital representation of a different patient-specific prosthetic template from the plurality of patient-specific prosthetic templates and can represent a degree of accuracy between the digital representation of that patient-specific prosthetic template and the second digital representation of the anatomic imaging data. Thus, in some instances, a user can select a digital representation of the prosthetic template with the highest score suitable for a patient.

Any of the embodiments described herein can be configured to define a modified representation of a portion of a patient's anatomy based on data associated with any suitable set of characteristics associated with the patient, a prosthetic, a manner of delivery, and/or the like. In some embodiments, the data associated with the set of characteristics can be updated based on, for example, empirical data and/or the like. For example, in some embodiments, a value, weight, score, factor, and/or the like can be associated with each characteristic in the set of characteristics. In some instances, anatomic imaging data can be taken of the portion of the patient's anatomy after the delivery of a prosthetic and based on data included in the post-delivery anatomic imaging data the value, weight, score, factor, and/or the like associated with the set of characteristics can be updated. In this manner, the accuracy of a projected change in the portion of the anatomy as a result of the delivery and/or indwelling of a prosthetic can be increased based on adjusting and/or "tuning" the weight and/or influence of one or more characteristics associated with the patient, the prosthetic, and/or the delivery method.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™ Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, FORTRAN, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Some embodiments and/or methods described herein can be performed by software (executed on hardware), hardware, or a combination thereof and configured to process and/or execute one or more programs and/or instructions stored, for example, in memory. Specifically, some of the embodiments described such as the host device 120 can be configured to process and/or execute one or more programs associated with 3-D solid modeling, computer aided design (CAD), volume or surface reconstruction, image analysis and/or segmentation, and/or the like. Such programs can include but are not limited to, for example, MATLAB, TeraRecon, FreeCAD, SolidWorks, AutoCAD, Creo, and/or the like. Such programs can be used, for example, to identify features of interest, which can be traced with spline curves fit to user-specified points. In addition, indicators or markers can be placed at specific 3-D locations to indicate the origins of the branch vessels. In an embodiment, the outlines are converted to 3-D contours that define the feature locations in the 3-D space. The 3-D contours can be converted to a mesh to define a 3-D surface model. In some embodiments, segmentation software can be configured to obtain different types of imaging data such as CT imaging data, ultrasound data, and/or the like. In some embodiments, the size of the generated 3-D surface model can be modified to optimize the graft fenestration process. For example, the surface model may be radially expanded to add a predefined wall thickness to allow generation of a solid fenestration template.

In some embodiments such programs, can produce 3-D and multi-planar views of CT image sets. In some embodiments, such a visualization tool can perform automatic vessel boundary detection, which can be imported into segmentation software that generates the 3-D surfaces to expedite the model generation and hence the fenestration generation process. In some embodiments, such visualization tools can automatically generate 3-D surface data for a digital model and/or a fenestration template. Once the vessel boundaries are identified, corresponding openings in the 3-D digital model can be created and/or defined. In some embodiments, a subtraction between the solid part model and a cylinder with the desired fenestration diameter can define the openings in the 3-D digital model. In another embodiment, holes representing the origins of branch vessels may be added using a CAD program such as those listed above. In some embodiments, a 3-D digital model is converted to a solid object model format such as stereolithography (STL) or Virtual Reality Modeling Language (VRML) that is supported by a 3-D printer or similar template generation device. Advantageously, the availability of automatic aorta boundary detection makes the creation of the present fenestration template a practical option for routine use in endovascular aortic aneurysm repair. Raw imaging data or the segmented aorta boundaries and fenestration locations may be sent to an outside processing facility, and the fenestration template shipped back to the surgery site. Therefore, individual clinical sites not employ individuals with expertise in image segmentation, CAD software, and/or 3-D output devices.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

What is claimed:

1. A device for locating a fenestration position on a stent graft, the device comprising:
   a) a patient-specific fenestration template configured to be coupled to the stent graft, the patient-specific fenestration template representing a portion of a patient's aorta, the portion of the patient's aorta having a first branch blood vessel extending from the aorta and a second branch blood vessel extending from the aorta,
   b) the patient-specific fenestration template having a first marker corresponding to a predicted location of the first branch blood vessel, and a second marker corresponding to a predicted location of the second branch blood vessel;
      wherein the predicted location of the first marker is based on a modified digital representation of the portion of the aorta including:
         data representative of a first location of the first branch blood vessel, and data representative of a second location of the first branch blood vessel, the second location of the first branch blood vessel is different than the first location of the first blood vessel.

2. The device of claim 1, wherein the portion of the patient's aorta has a first configuration, and the modified digital representation of the portion of the patient's aorta is associated with a second configuration of the portion of the patient's aorta, the portion of the patient's aorta being transitioned from the first configuration to the second configuration in response to insertion of the stent graft.

3. The device of claim 2, wherein the modified digital representation of the portion of the patient's aorta is based on a centerline of the portion of the patient's aorta in the second configuration.

4. The device of claim 3, wherein the predicted location of the first marker and the predicted location of the second marker is determined based on the centerline of the portion of the patient's aorta in the second configuration.

5. The device of claim 1, wherein the patient-specific fenestration template is hollow.

6. The device of claim 5, wherein the patient-specific fenestration template is configured to receive a stent graft within a lumen thereof.

7. The device of claim 1, wherein the patient-specific fenestration template is substantially annular.

8. The device of claim 1, wherein the first branch blood vessel corresponds to a renal artery.

9. The device of claim 1, wherein the diameter of a first fenestration corresponds to a diameter of the first branch blood vessel.

10. The device of claim 1, wherein the predicted location of the second marker is based on a modified digital representation of the portion of the aorta including: data representative of a first location of the second branch blood vessel, and data representative of a second location of the second branch blood vessel, the second location of the second branch blood vessel is different than the first location of the second blood vessel.

\* \* \* \* \*